(12) United States Patent
Okada

(10) Patent No.: US 11,492,441 B2
(45) Date of Patent: Nov. 8, 2022

(54) BLOCKED ISOCYANATE, PHOTO-CURABLE COMPOSITION, RESIN, AND METHOD OF MANUFACTURING THREE-DIMENSIONAL OBJECT

(71) Applicant: CANON KABUSHIKI KAISHA, Tokyo (JP)

(72) Inventor: Seiji Okada, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 838 days.

(21) Appl. No.: 16/190,637

(22) Filed: Nov. 14, 2018

(65) Prior Publication Data

US 2019/0161573 A1    May 30, 2019

(30) Foreign Application Priority Data

Nov. 27, 2017    (JP) .............................. JP2017-226771

(51) Int. Cl.
| | | |
|---|---|---|
| C08G 18/81 | (2006.01) | |
| C07C 275/60 | (2006.01) | |
| C08G 18/38 | (2006.01) | |
| C07C 275/14 | (2006.01) | |
| B33Y 70/00 | (2020.01) | |
| C08G 18/67 | (2006.01) | |
| C08G 18/48 | (2006.01) | |
| C08G 18/24 | (2006.01) | |
| C08G 18/78 | (2006.01) | |
| C08G 18/28 | (2006.01) | |
| C08F 290/06 | (2006.01) | |
| C08G 18/73 | (2006.01) | |
| C08G 18/10 | (2006.01) | |
| C08G 18/32 | (2006.01) | |
| C08G 18/44 | (2006.01) | |
| C08G 18/42 | (2006.01) | |

(Continued)

(52) U.S. Cl.
CPC ............ *C08G 18/815* (2013.01); *B33Y 70/00* (2014.12); *C07C 275/14* (2013.01); *C07C 275/60* (2013.01); *C08F 290/067* (2013.01); *C08G 18/10* (2013.01); *C08G 18/244* (2013.01); *C08G 18/2895* (2013.01); *C08G 18/3243* (2013.01); *C08G 18/3819* (2013.01); *C08G 18/42* (2013.01); *C08G 18/44* (2013.01); *C08G 18/48* (2013.01); *C08G 18/4854* (2013.01); *C08G 18/672* (2013.01); *C08G 18/73* (2013.01); *C08G 18/7837* (2013.01); *B29C 64/135* (2017.08); *B29K 2075/00* (2013.01); *B29K 2096/04* (2013.01); *B33Y 10/00* (2014.12); *C07C 2601/14* (2017.05)

(58) Field of Classification Search
CPC ...... C08G 18/815; C08G 18/42; C08G 18/44; C08G 18/48; C08G 18/10; C08G 18/244; C08G 18/2895; C08G 18/3243; C08G 18/3819; C08G 18/4854; C08G 18/672; C08G 18/73; C08G 18/7837; B33Y 70/00; B33Y 10/00; C07C 275/14; C07C 275/60; C07C 2601/14; C08F 290/067; B29K 2096/04; B29K 2075/00; B29C 64/135
See application file for complete search history.

(56) References Cited

FOREIGN PATENT DOCUMENTS

| | | |
|---|---|---|
| JP | 2017-524565 A | 8/2017 |
| JP | 2017-527637 A | 9/2017 |

(Continued)

OTHER PUBLICATIONS

Notice of Reasons for Refusal in Japanese Application No. 2017-226771 (dated Sep. 2021).

*Primary Examiner* — Rabon A Sergent

(74) *Attorney, Agent, or Firm* — Venable LLP

(57) ABSTRACT

Provided is a photo-curable composition capable of creating a three-dimensional object excellent in both of: stiffness and strength; and toughness. Specifically, provided is a photo-curable composition including: a blocked isocyanate represented by the general formula (1); a chain extender; and a photo-radical generator:

$$A_1 \diagdown_{\displaystyle B}\diagup A_3 \atop A_2 \diagup {}^{\displaystyle}\diagdown A_4 \quad (1)$$

wherein, in the general formula (1), $A_1$ to $A_4$ each independently represent a structure represented by the following general formula (2), and B represents a structure represented by the following general formula (3)

$$R_1\!-\!\!\underset{\underset{}{}}{\overset{\overset{O}{\|}}{C}}\!-\!O\!-\!L_1\!-\!\underset{\underset{R_2}{|}}{N}\!\!\sim\!\!\sim \quad (2)$$

(Continued)

-continued

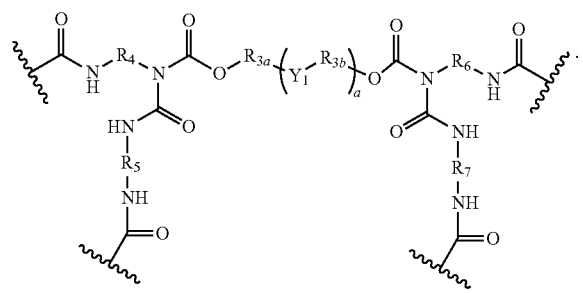
(3)

10 Claims, 1 Drawing Sheet

(51) Int. Cl.
*B29K 96/04* (2006.01)
*B29C 64/135* (2017.01)
*B33Y 10/00* (2015.01)
*B29K 75/00* (2006.01)

(56) References Cited

FOREIGN PATENT DOCUMENTS

| WO | 2015/200173 A1 | 12/2015 |
| WO | 2015/200179 A1 | 12/2015 |
| WO | 2015/200189 A1 | 12/2015 |
| WO | 2015/200201 A1 | 12/2015 |
| WO | 2017/112653 A1 | 6/2017 |

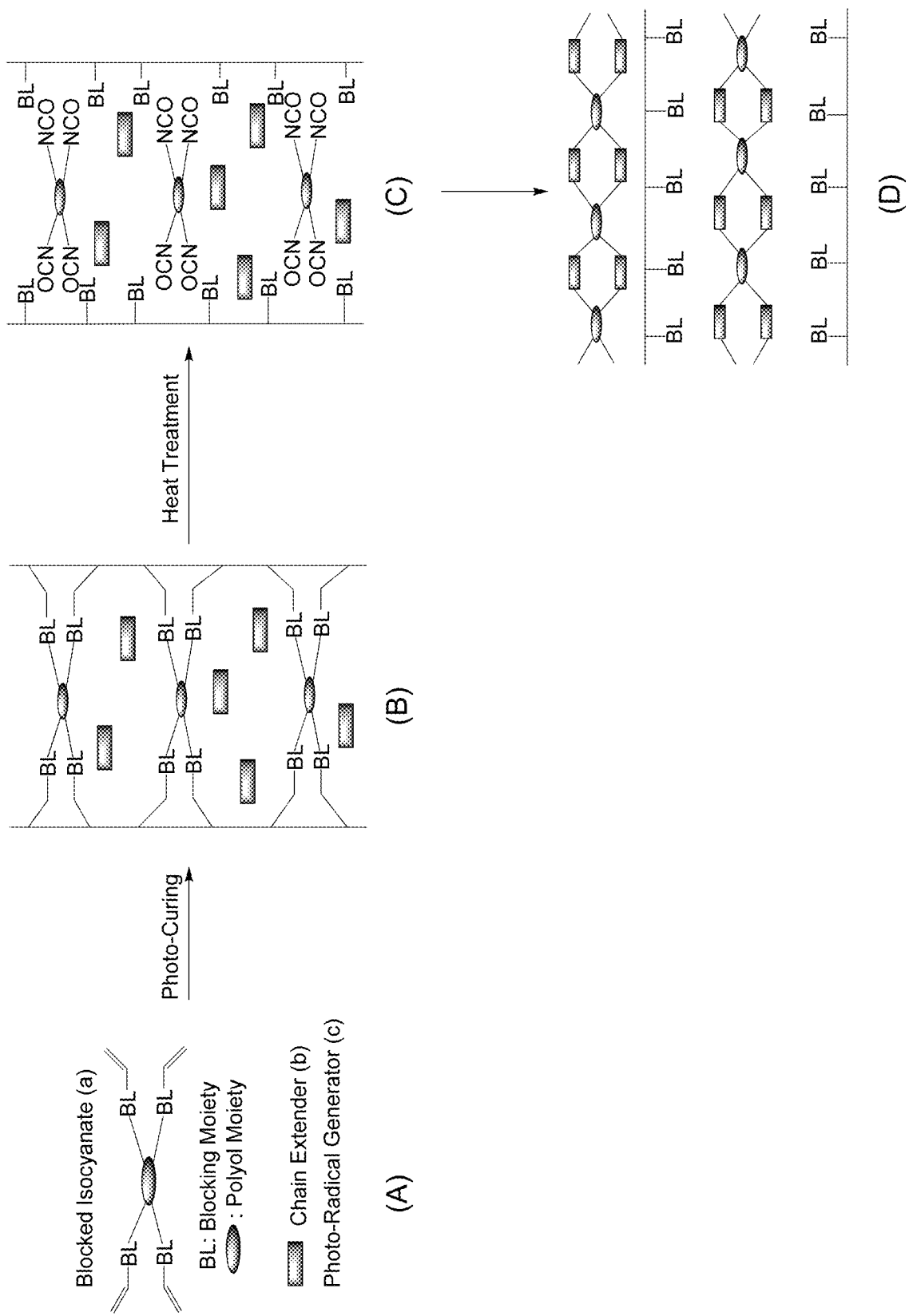

BLOCKED ISOCYANATE, PHOTO-CURABLE COMPOSITION, RESIN, AND METHOD OF MANUFACTURING THREE-DIMENSIONAL OBJECT

BACKGROUND OF THE INVENTION

Field of the Invention

The present invention relates to a blocked isocyanate, a photo-curable composition, a resin, and a method of manufacturing a three-dimensional object.

Description of the Related Art

Stereolithography involving curing a liquid photo-curable composition with light, such as an ultraviolet ray, layer by layer and laminating the layers sequentially to produce a desired three-dimensional object has been extensively investigated. The applications of the stereolithography are not exclusive to creation of a prototype (rapid prototyping) for shape confirmation, and have extended to, for example, creation of a working model or a mold (rapid tooling) for functional verification. In addition, the applications of the stereolithography are extending also to creation of an actual product (rapid manufacturing).

Under the above-mentioned background, there has been a high degree of demand for a photo-curable composition for creating a three-dimensional object to be used for the stereolithography. Recently, a photo-curable composition for creating a three-dimensional object capable of creating a three-dimensional object having high mechanical characteristics (e.g., strength and stiffness, and toughness) comparable to those of generally used engineering plastic has been required.

In International Publication No. WO2015/200201, there is a description of a method of creating a three-dimensional object including performing stereolithographic creation (photo-curing) through use of a photo-curable composition including: a blocked isocyanate having an acrylic group; and a chain extender, and subjecting the resultant photo-cured object to heat treatment. According to the method described in International Publication No. WO2015/200201, a three-dimensional object balanced in, for example: stiffness and strength; and toughness is obtained.

With the photo-curable composition described in International Publication No. WO2015/200201, a cured product more balanced in, for example: stiffness and strength; and toughness than that obtained with a related-art photo-curable composition, such as a urethane-acrylate photo-curable composition, is obtained through the heat treatment after the photo-curing. However, the photo-curable composition has a problem in that toughness is reduced when stiffness or strength is to be increased.

SUMMARY OF THE INVENTION

In view of the above-mentioned problem, an object of the present invention is to provide a photo-curable composition capable of creating a three-dimensional object excellent in both of: stiffness and strength; and toughness.

According to one embodiment of the present invention, there is provided a blocked isocyanate represented by the general formula (1):

in the general formula (1), $A_1$ to $A_4$ each independently represent a structure represented by the following general formula (2), and B represents a structure represented by the following general formula (3);

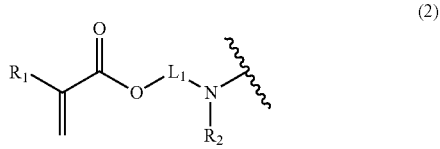

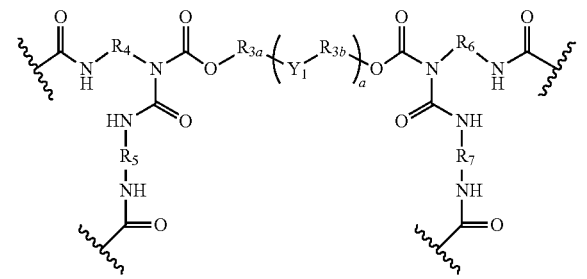

in the general formula (2), $R_1$ represents a hydrogen atom or a methyl group, $R_2$ represents a hydrocarbon group having 1 to 10 carbon atoms which may have a substituent, and $L_1$ represents a divalent hydrocarbon group having 1 to 10 carbon atoms which may have a substituent;

in the general formula (3), $R_{3a}$, $R_{3b}$, $R_4$, $R_5$, $R_6$, and $R_7$ each independently represent a divalent hydrocarbon group having 1 to 20 carbon atoms which may have a substituent, $Y_1$ represents a divalent linking group, and "a" represents an integer of 1 or more and 99 or less.

According to the blocked isocyanate according to the one embodiment of the present invention, a photo-curable composition for creating a three-dimensional object capable of creating a three-dimensional object having higher toughness than in the related-art can be provided.

Further features of the present invention will become apparent from the following description of exemplary embodiments with reference to the attached drawing.

BRIEF DESCRIPTION OF THE DRAWINGS

FIG. 1s a view for schematically illustrating a reaction scheme in which a photo-curable composition according to an embodiment of the present invention is irradiated with light to be cured, and is then subjected to heat treatment.

DESCRIPTION OF THE EMBODIMENTS

Preferred embodiments of the present invention will now be described in detail in accordance with the accompanying drawing.

Now, embodiments of the present invention are described. The present invention is not limited to the following embodiments, and an embodiment obtained by, for example, appropriately changing or improving each of the following embodiments within a range not departing from the gist of the present invention based on general knowledge of a person skilled in the art is also encompassed in the scope of the present invention.

First Embodiment

A blocked isocyanate according to this embodiment is a blocked isocyanate represented by the general formula (1):

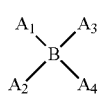
(1)

in the general formula (1), $A_1$ to $A_4$ each independently represent a structure represented by the following general formula (2), and B represents a structure represented by the following general formula (3);

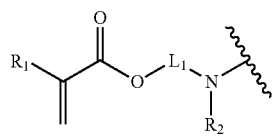
(2)

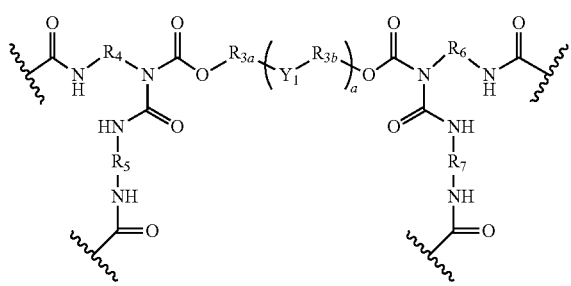
(3)

in the general formula (2), $R_1$ represents a hydrogen atom or a methyl group, $R_2$ represents a hydrocarbon group having 1 to 10 carbon atoms which may have a substituent, and $L_1$ represents a divalent hydrocarbon group having 1 to 10 carbon atoms which may have a substituent;
in the general formula (3), $R_{3a}$, $R_{3b}$, $R_4$, $R_5$, $R_6$, and $R_7$ each independently represent a divalent hydrocarbon group having 1 to 20 carbon atoms which may have a substituent, $Y_1$ represents a divalent linking group, and "a" represents an integer of 1 or more and 99 or less.

As described above, the blocked isocyanate is a (meth) acrylic compound having at least four (meth)acryloyl groups. The "(meth)acryloyl group" as used herein means an acryloyl group or a methacryloyl group, and the "(meth) acrylic compound" as used herein means an acrylic compound or a methacrylic compound. The (meth)acryloyl group is a polymerizable functional group, and the blocked isocyanate is subjected to a polymerization reaction through a radical generated from a photo-radical generator described below.

When any one of $L_1$, $R_2$, $R_{3a}$, $R_{3b}$, $R_4$, $R_5$, $R_6$, and $R_7$ in the general formula (2) and general formula (3) has a substituent, the substituent may be a substituent including a carbon atom. However, in such case, an atom of the substituent which is bonded to each of $L_1$, $R_2$, $R_{3a}$, $R_{3b}$, $R_4$, $R_5$, $R_6$, and $R_7$ is an atom other than the carbon atom. In addition, in such case, the number of carbon atoms included in the substituent is not included in the number of carbon atoms of the "hydrocarbon group".

In the general formula (2), $R_2$ preferably represents a group selected from the group consisting of a tert-butyl group, a tert-pentyl group, and a tert-hexyl group. When the those groups are used, it is preferred because a temperature (deblocking temperature) at which a photo-curable composition having been photo-cured is subjected to heat treatment to be deblocked can be reduced. In addition, when any one of the above-mentioned groups is adopted as $R_2$, the blocked isocyanate can be synthesized easily. In addition, when any one of the above-mentioned groups is adopted as $R_2$, the blocked isocyanate can be synthesized at low cost.

In the general formula (2), $L_1$ preferably represents an ethylene group or a propylene group from the viewpoints of easy availability and easy synthesis.

In the general formula (3), $Y_1$ preferably represents at least one divalent linking group selected from the group consisting of groups represented by the following formulae (B1) to (B3) from the viewpoints of easy availability and easy synthesis.

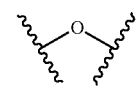
(B1)

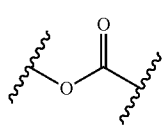
(B2)

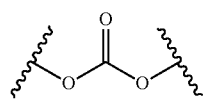
(B3)

In addition, in the general formula (1), $A_1$ to $A_4$ are preferably identical to one another. That is, the blocked isocyanate is preferably represented by the following general formula (I). With this, the blocked isocyanate can be synthesized easily at low cost.

(I)

In the general formula (I), A represents a group represented by the general formula (2), and "B" represents a group represented by the general formula (3).

As a specific structure of the blocked isocyanate, there are given, for example, blocked isocyanates represented by the following formulae (I-1) to (I-21).

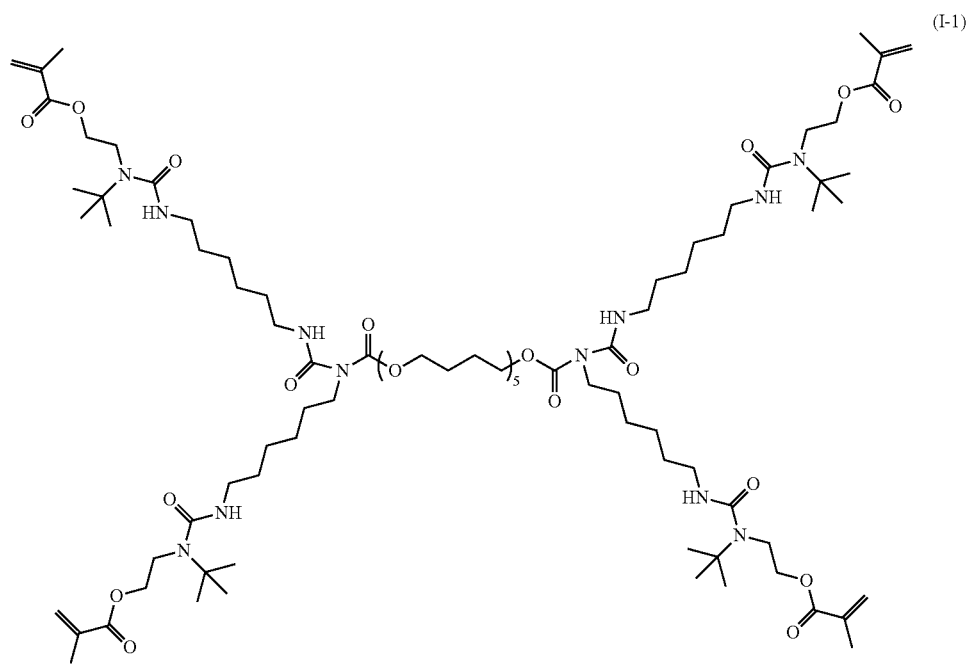
(I-1)
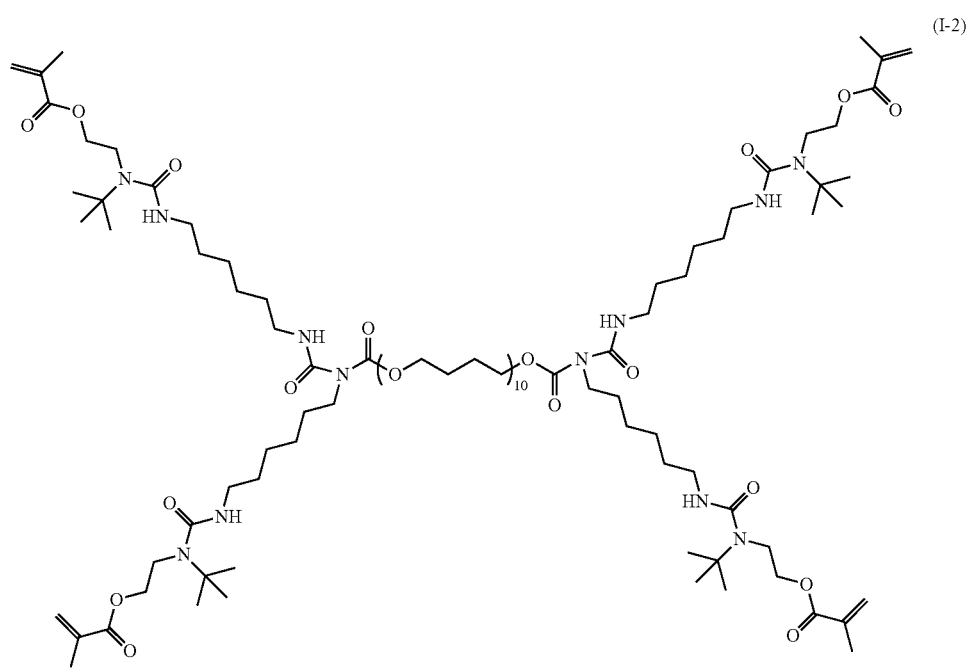
(I-2)

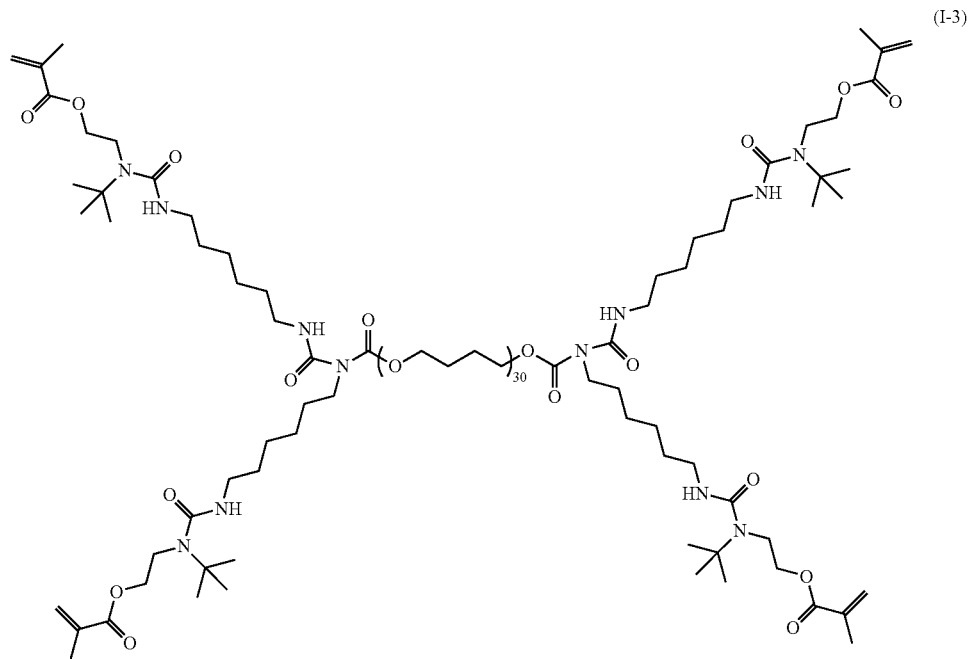
(I-3)
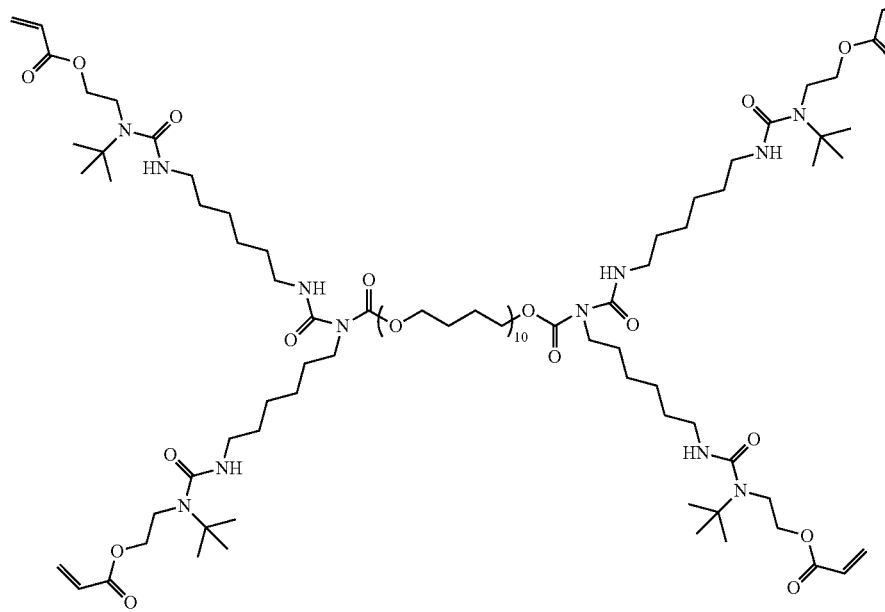
(I-4)

-continued
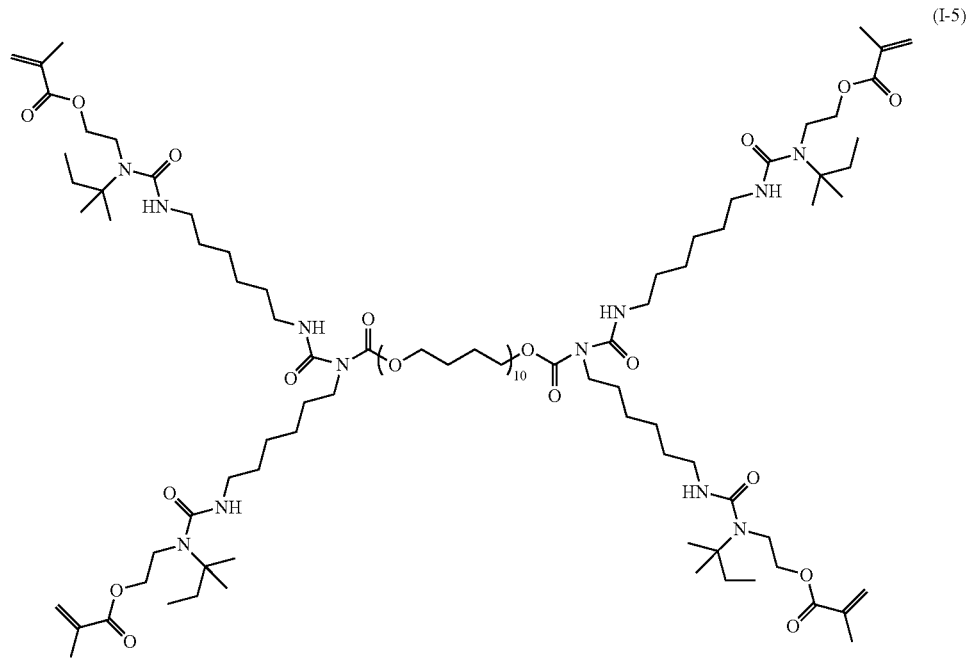
(I-5)
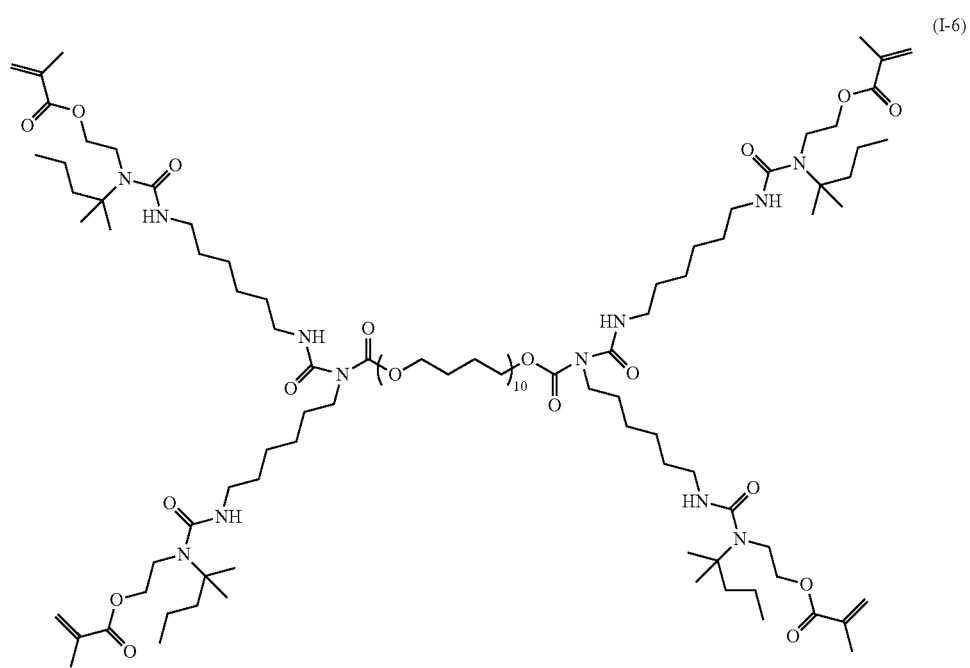
(I-6)

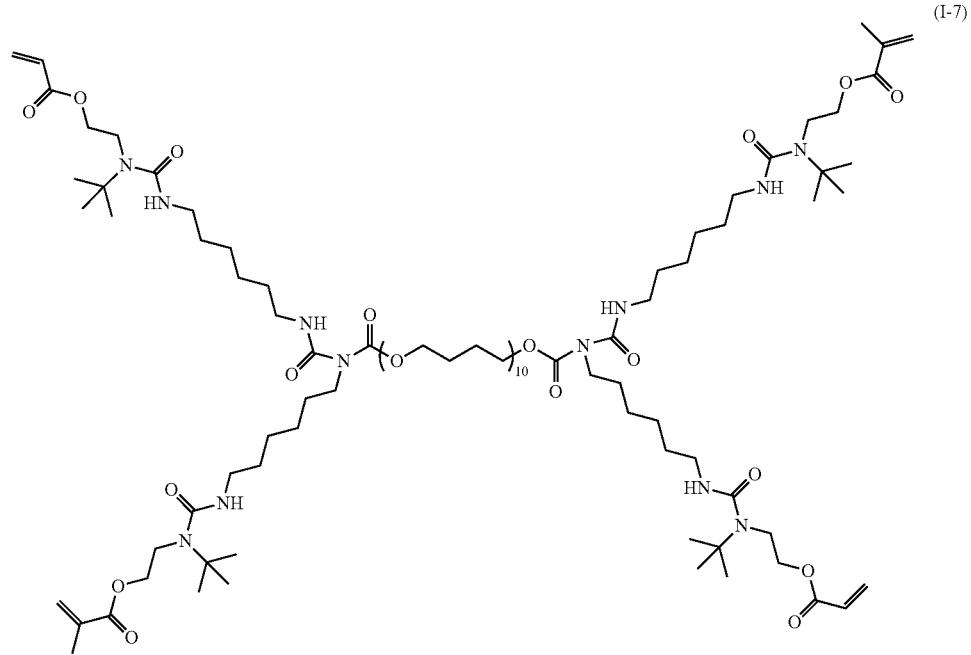
(I-7)
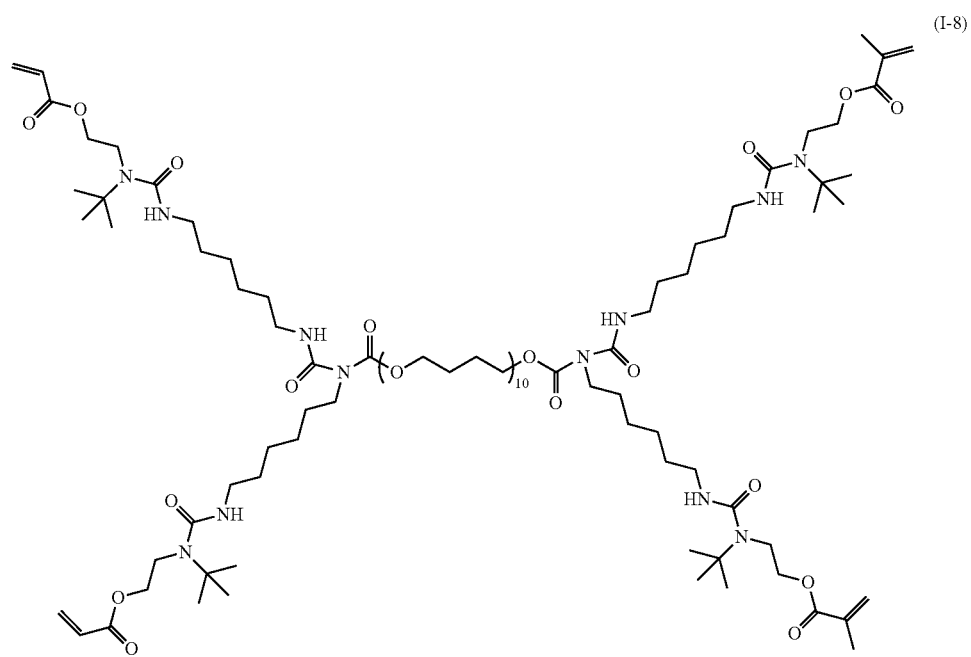
(I-8)

-continued
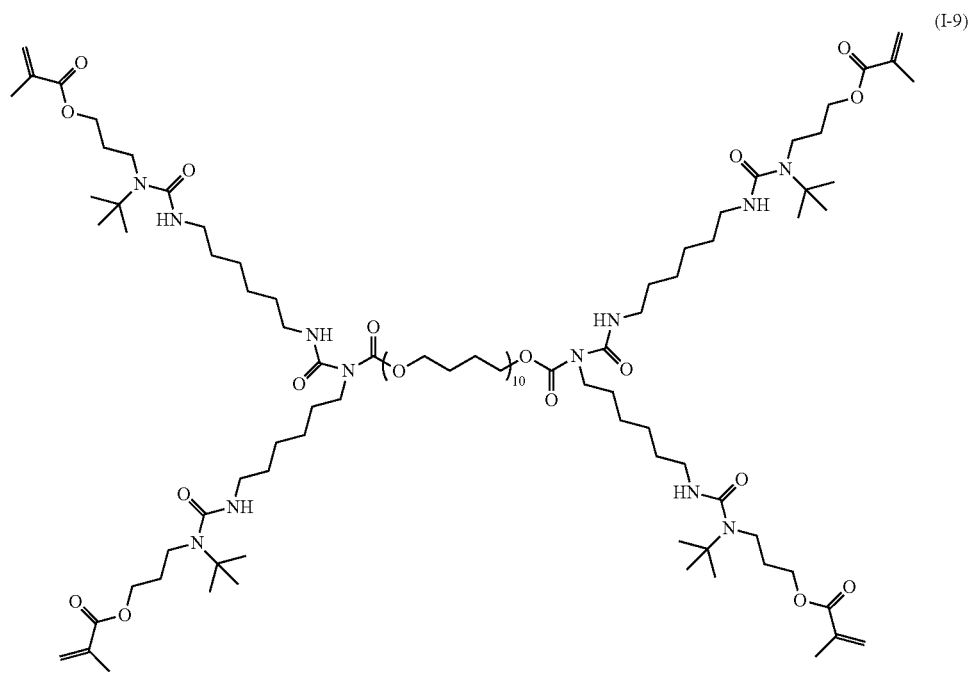
(I-9)
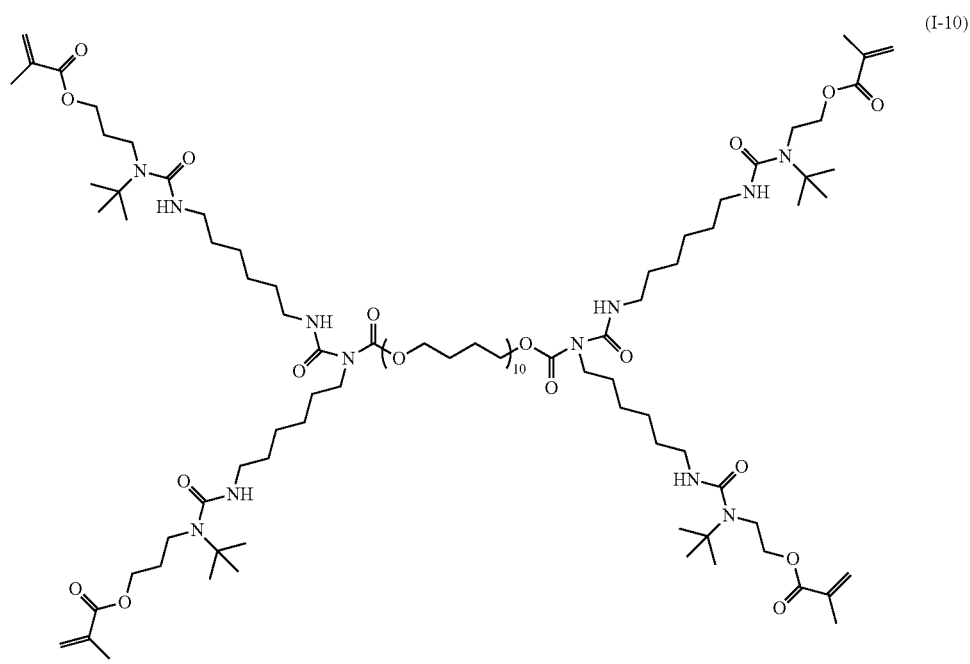
(I-10)

(I-11)
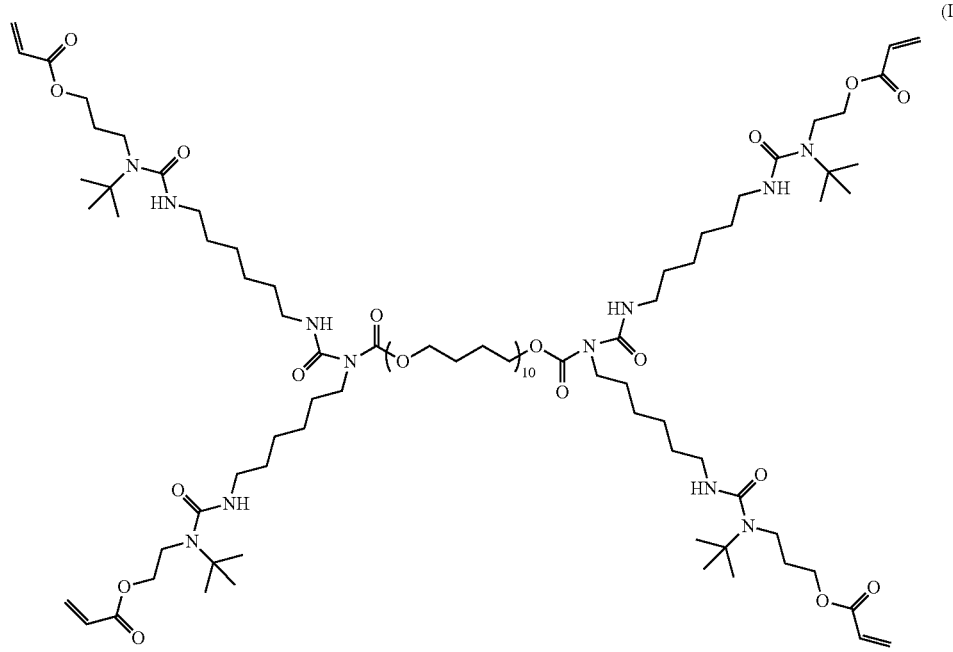
(I-12)
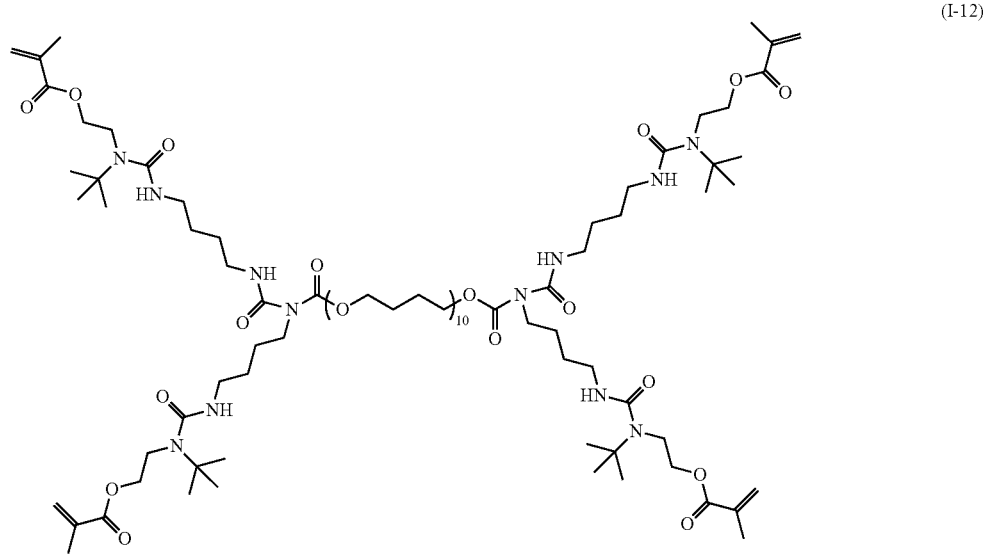

-continued
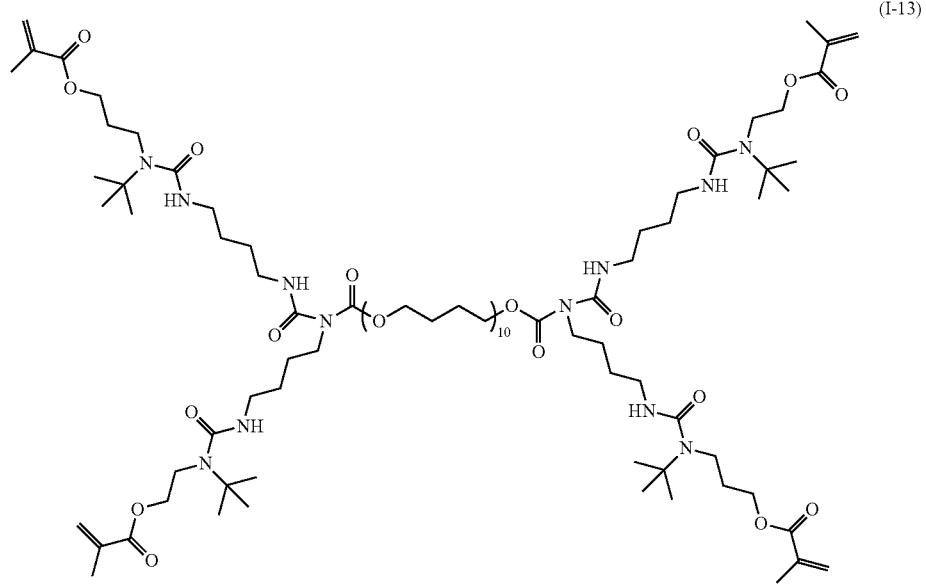
(I-13)
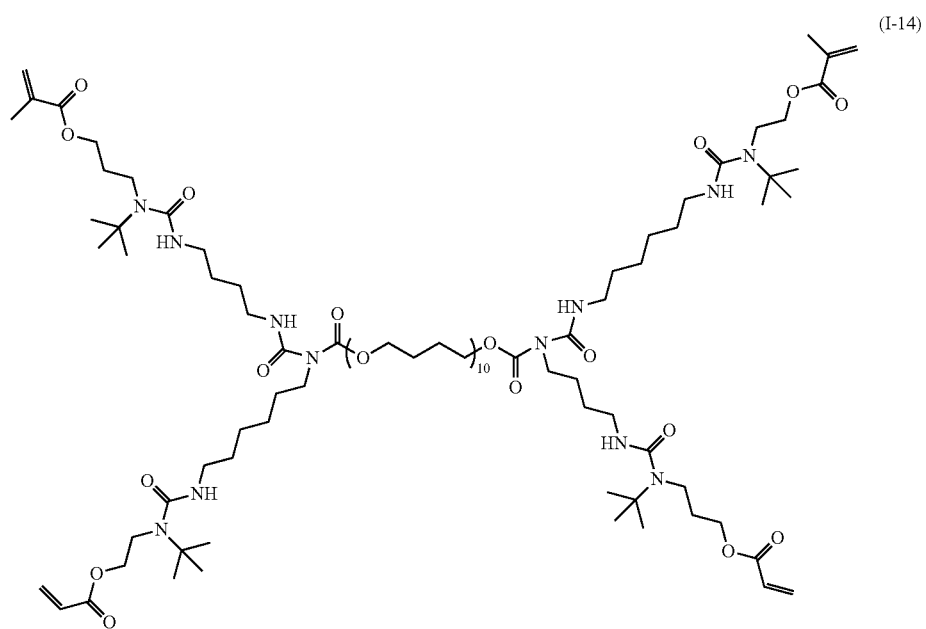
(I-14)

(I-15)
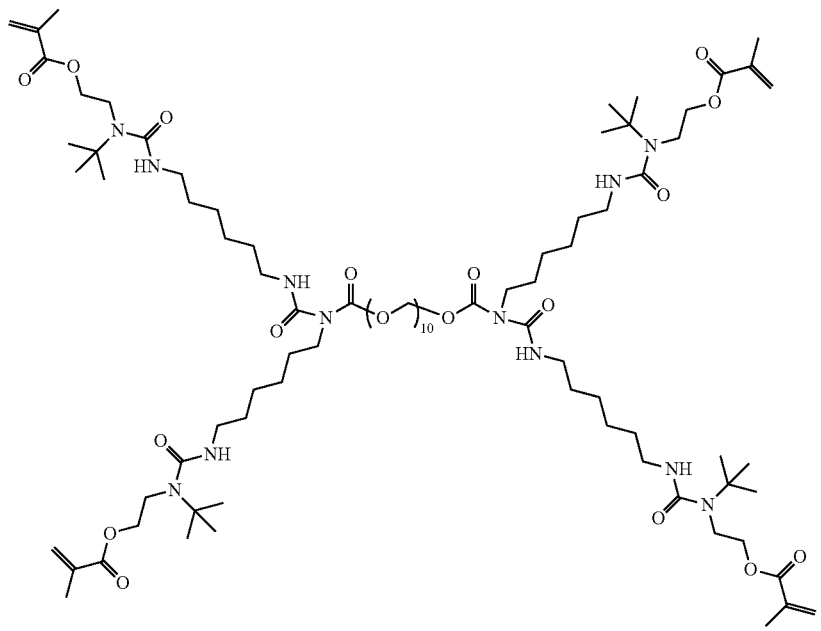
(I-16)
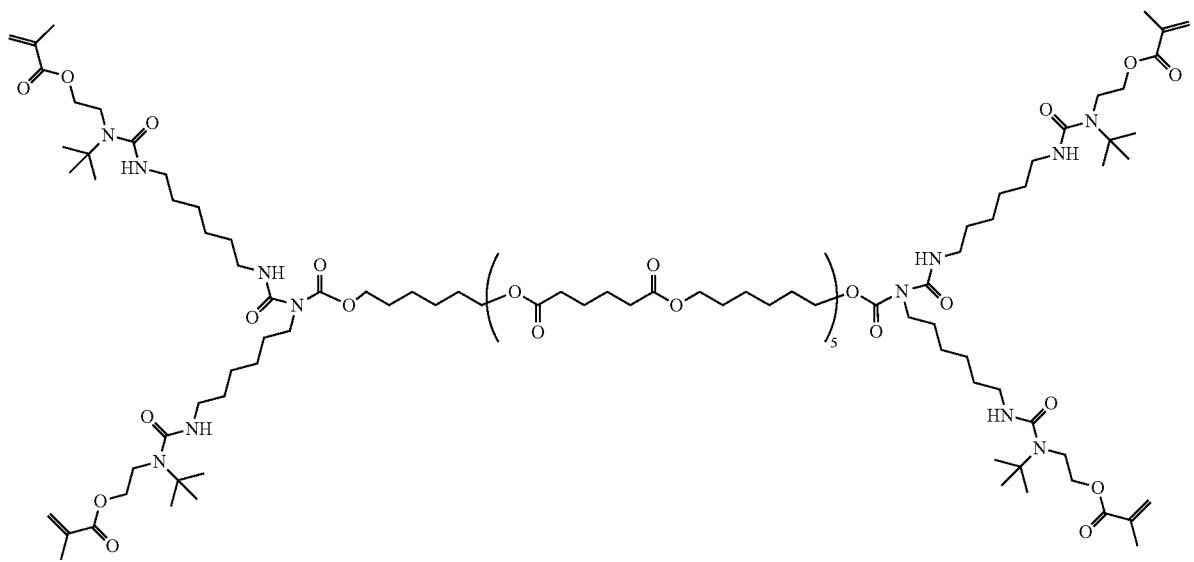

(I-17)
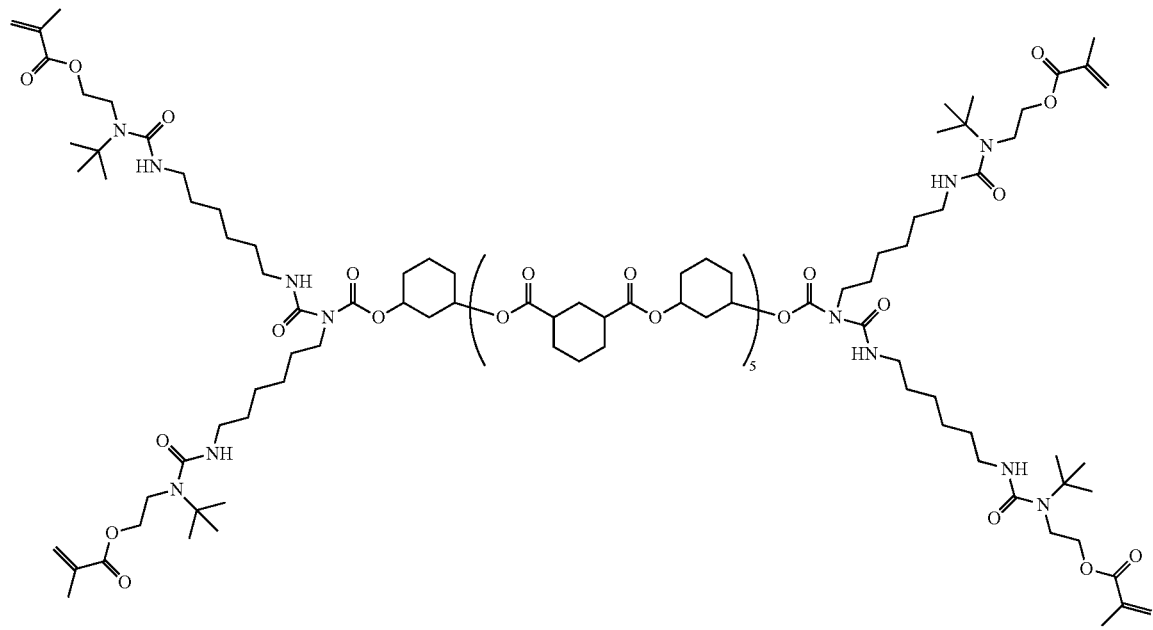
(I-18)
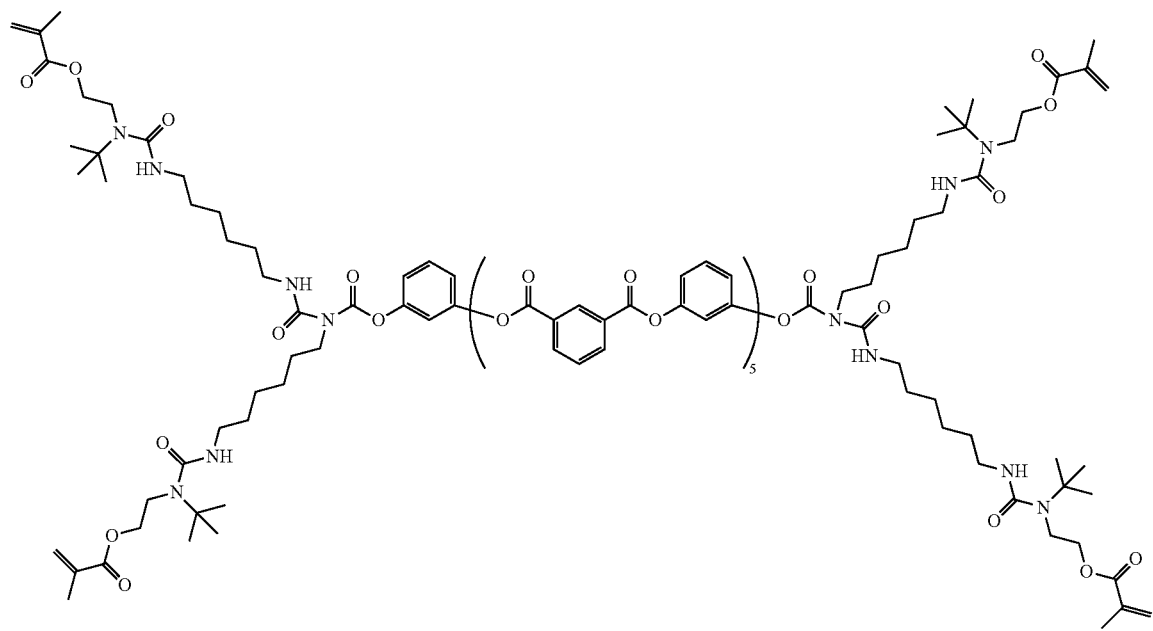

(I-19)
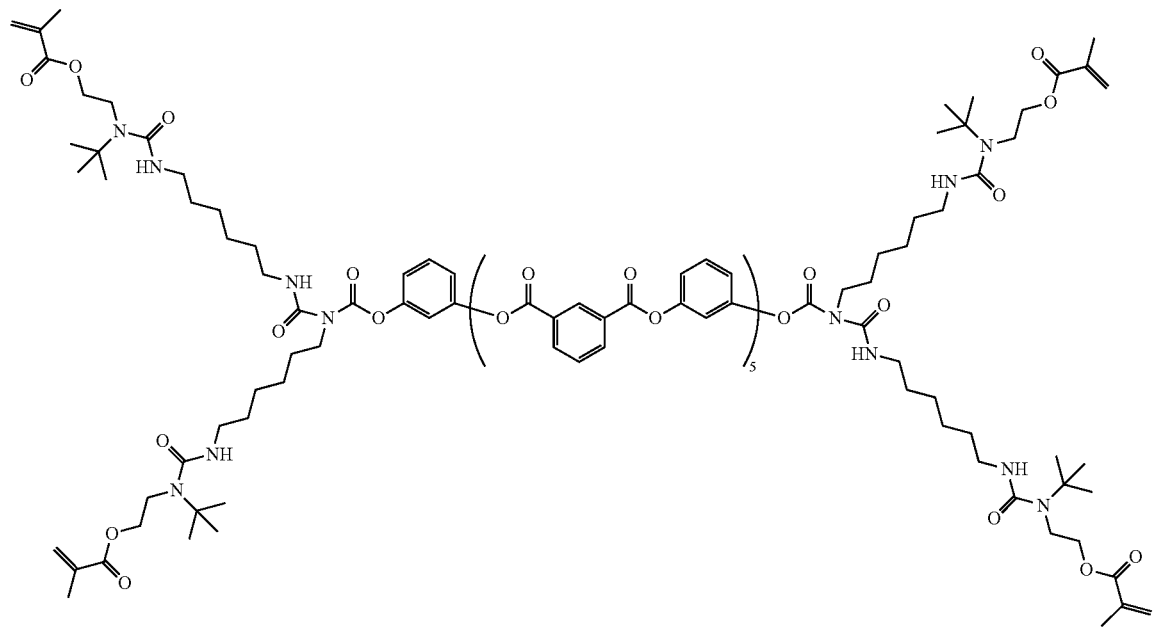
(I-20)
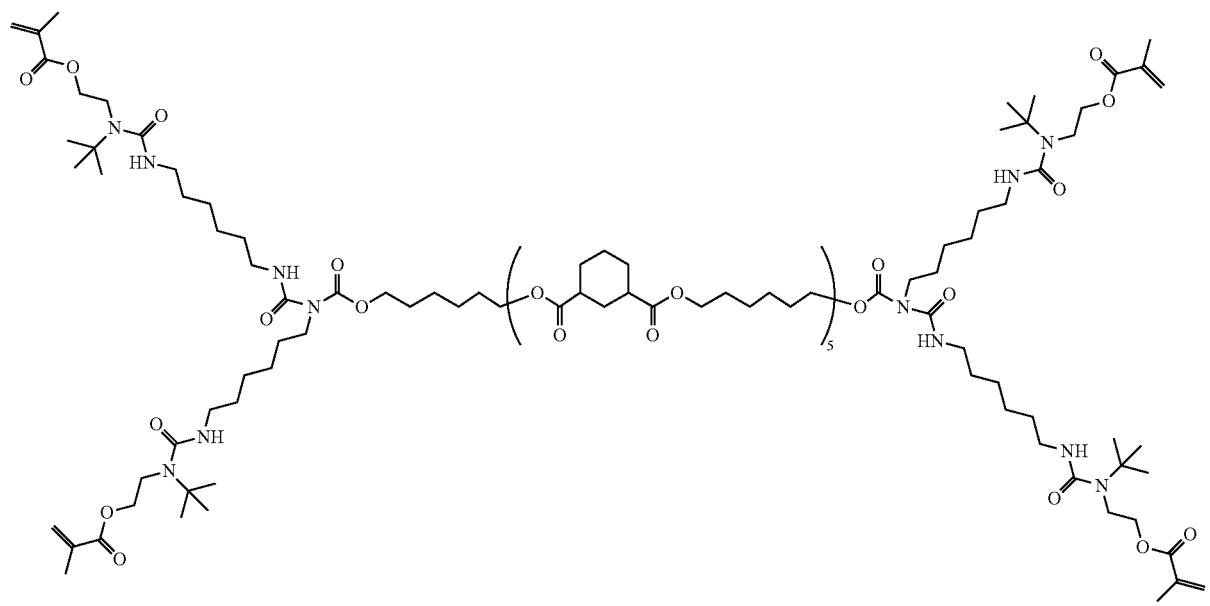

(I-21)

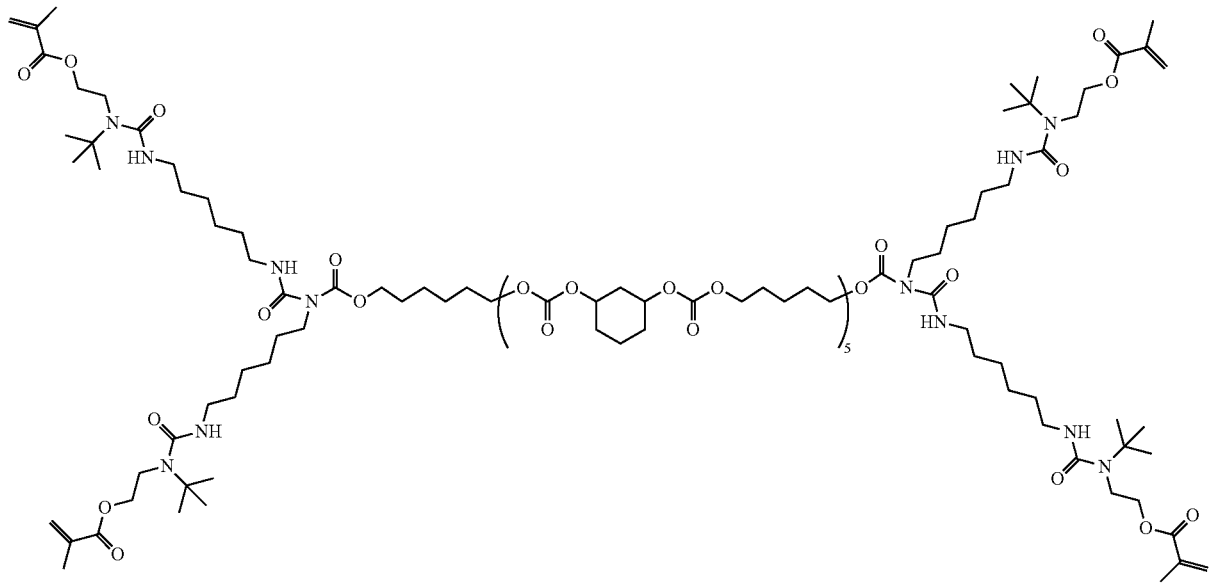

<Synthesis Method for Blocked Isocyanate>

Next, a synthesis method for the blocked isocyanate is described. The synthesis method for the blocked isocyanate includes a step (I) and a step (II) described below.

Step (I): a step of subjecting a polyol and a diisocyanate to a reaction

Step (II): a step of subjecting a blocking agent and a tetraisocyanate having a polyol skeleton obtained by the step (I) to a reaction Each of the steps is described below.

(Step (I): Step of Subjecting Polyol and Diisocyanate to Reaction)

This step is a step of subjecting a polyol and a diisocyanate to a reaction. With this, a tetraisocyanate having a polyol skeleton is obtained.

The polyol to be used in this step is a compound having hydroxyl groups at both ends of a polymer. Examples thereof include, but are not limited to, a polyether polyol, a polyester polyol, a polycarbonate polyol, and a polyacetal. Those polyols may be used as a mixture thereof.

The polyol preferably has a number average molecular weight Mn of 100 or more and 5,000 or less. When the polyol has a number average molecular weight Mn of less than 100, the molecular weight of the finally obtained blocked isocyanate is reduced. As a result, there is a risk in that a photo-cured/thermally cured product described below is reduced in elongation, and reduced in impact resistance. When the polyol has a number average molecular weight Mn of more than 5,000, the molecular weight of the finally obtained blocked isocyanate is increased. As a result, there is a risk in that a curable composition is increased in viscosity, and thus operability is reduced, or the photo-cured/thermally cured product described below is reduced in modulus of elasticity.

Examples of the diisocyanate to be used in this step include, but are not limited to: aliphatic diisocyanates, such as trimethylene diisocyanate, 1,2-propylene diisocyanate, butylene diisocyanate, hexamethylene diisocyanate, pentamethylene diisocyanate, and trimethylhexamethylene diisocyanate; alicyclic diisocyanates, such as cyclohexane diisocyanate, methylcyclohexane diisocyanate, 3-isocyanatomethyl-3,5,5-trimethylcyclohexyl isocyanate (isophorone diisocyanate), methylenebis(cyclohexyl isocyanate) or dicyclohexylmethane diisocyanate, bis(isocyanatomethyl)cyclohexane, and norbornane diisocyanate; and aromatic diisocyanates, such as phenylene diisocyanate, tolylene diisocyanate, 4,4'-diphenyl diisocyanate, 1,5-naphthalene diisocyanate, diphenylmethane diisocyanate, and 4,4'-toluidine diisocyanate.

In this step, the polyol and the diisocyanate are preferably subjected to a reaction in a solvent. The solvent is not particularly limited as long as the polyol and the diisocyanate are dissolved therein. Specific examples thereof include: dialkyl ethers, such as diethyl ether and dipropyl ether; cyclic ethers, such as 1,4-dioxane and tetrahydrofuran; ketones, such as acetone, methyl ethyl ketone, diisopropyl ketone, and isobutyl methyl ketone; esters, such as methyl acetate, ethyl acetate, and butyl acetate; hydrocarbons, such as toluene, xylene, and ethylbenzene; halogen-based solvents, such as methylene chloride, chloroform, carbon tetrachloride, tetrachloroethane, trichloroethane, and chlorobenzene; and nitriles, such as acetonitrile. Those solvents may be used alone or in combination thereof. In addition, as the solvent, a dehydrated solvent is preferably used from the viewpoint of suppressing decomposition of an isocyanate group of the diisocyanate caused by water.

A ratio of the number of moles of the diisocyanate to the number of moles of the polyol to be subjected to a reaction in this step, (number of moles of the diisocyanate/number of moles of the polyol), is preferably 4 or more and 20 or less, more preferably 8 or more and 15 or less. When the ratio is less than 4, a ratio of a diisocyanate is increased as compared to a ratio of a target tetraisocyanate having a polyol skeleton, and the yield of the target tetraisocyanate is reduced. When the ratio is more than 20, the diisocyanate, which is a raw material, remains unreacted excessively after the reaction, and it becomes difficult to remove the unreacted diisocyanate in some cases.

This step is preferably performed in an inert atmosphere, such as nitrogen, helium, or argon. In addition, this step is performed at preferably 10° C. or more and 150° C. or less, more preferably 40° C. or more and 100° C. or less. In addition, this step may be performed under reflux. When this step is performed at a reaction temperature of more than 150° C., there is an increased risk of occurrence of a side reaction. When this step is performed at a reaction temperature of less than 10° C., a reaction speed is reduced, and hence a reaction time period is prolonged or the yield is reduced.

This step may be performed under the presence of a catalyst. Examples of the catalyst include: organic tin-based compounds, such as tin octylate, dibutyltin diacetate, dibutyltin dilaurate, and tin 2-ethylhexanoate; naphthenic acid metal salts, such as copper naphthenate, zinc naphthenate, and cobalt naphthenate; and tertiary amines, such as triethylamine, benzyldimethylamine, pyridine, N,N-dimethylpiperazine, and triethylenediamine. Those catalysts may be used alone or in combination thereof. The amount of the catalyst to be used may be 0.001 mass % or more and 1 mass % or less with respect to 100 mass % of a total amount of the polyol.

The tetraisocyanate having a polyol skeleton obtained by this step may be separated and purified by a conventional separation method involving, for example, separation means, such as reprecipitation with a poor solvent, concentration, or filtration, or combination separation means thereof.

(Step (II): Step of Subjecting Blocking Agent and Tetraisocyanate Having Polyol Skeleton Obtained by Step (I) to Reaction)

This step is a step of subjecting a blocking agent and the tetraisocyanate having a polyol skeleton obtained by the step (I) to a reaction. With this, the blocked isocyanate according to this embodiment is obtained.

The "blocking agent" as used herein refers to a compound which can react with an isocyanate group (—NCO) of the tetraisocyanate to protect the active isocyanate group. The isocyanate group protected with the blocking agent is called a blocked isocyanate group. The blocked isocyanate group, which is protected with the blocking agent, can be kept stable under a normal state.

When a blocked isocyanate compound having a blocked isocyanate group is heated, the blocking agent dissociates from the blocked isocyanate group (deblocking), and the original isocyanate group can be regenerated.

The blocking agent to be used in this step is not particularly limited as long as the blocking agent is a (meth)acrylic compound having an amino group, but is preferably a compound selected from tert-butylaminoethyl (meth)acrylate, tert-pentylaminoethyl (meth)acrylate, tert-hexylaminoethyl (meth)acrylate, and tert-butylaminopropyl (meth)acrylate. With this, a deblocking temperature of the blocked isocyanate can be reduced.

In this step, the blocking agent and the tetraisocyanate having a polyol skeleton are preferably subjected to a reaction in a solvent. The solvent is not particularly limited as long as the blocking agent and the tetraisocyanate having a polyol skeleton are dissolved therein. Specifically, the solvents described in the step (I) may be used.

This step is preferably performed in an inert atmosphere, such as nitrogen, helium, or argon. In addition, this step is performed at preferably 0° C. or more and 150° C. or less, more preferably 50° C. or more and 100° C. or less. In addition, this step may be performed under reflux. When this step is performed at a reaction temperature of less than 0° C., the reaction is difficult to proceed. In addition, when this step is performed at a reaction temperature of more than 150° C., there is a risk in that the blocking agents are polymerized with each other through a polymerization reaction between (meth)acryloyl groups. As a result, there is a risk in that the yield is reduced.

This step may be performed under the presence of a catalyst. As specific examples of the catalyst, the catalysts described in the step (I) may be used.

In addition, in this step, a polymerization inhibitor may be used for the purpose of suppressing the polymerization between (meth)acryloyl groups of the blocking agents. Specific examples thereof include benzoquinone, hydroquinone, catechol, diphenyl benzoquinone, hydroquinone monomethyl ether, naphthoquinone, t-butylcatechol, t-butylphenol, dimethyl-t-butylphenol, t-butylcresol, dibutylhydroxytoluene, and phenothiazine.

The blocked isocyanate obtained by this step may be separated and purified in the same manner as in the step (I).

Second Embodiment

A photo-curable composition according to a second embodiment of the present invention is described. The photo-curable composition according to this embodiment includes: a blocked isocyanate (a) according to the first embodiment; a chain extender (b); and a photo-radical generator (c).

The components included in the photo-curable composition according to this embodiment are described below in detail.

[Blocked Isocyanate (a)]

As the blocked isocyanate (a), the blocked isocyanate described in the first embodiment is used. As the blocked isocyanate (a) to be included in the photo-curable composition, one kind or a plurality of kinds of blocked isocyanates may be included. When a plurality of kinds of blocked isocyanates are included as the blocked isocyanate (a), the blending ratio of the blocked isocyanate (a) in the photo-curable composition is calculated based on a total mass of the plurality of kinds of blocked isocyanates.

The blending ratio of the blocked isocyanate (a) in the photo-curable composition is preferably 5 mass % or more and 90 mass % or less, more preferably 10 mass % or more and 70 mass % or less with respect to the entirety of the photo-curable composition. When the blending ratio is less than 5 mass %, a photo-cured product and a photo-cured/thermally cured product described below are reduced in modulus of elasticity and toughness. When the blending ratio is more than 90 mass %, the photo-curable composition is increased in viscosity, and its handling becomes difficult.

[Chain Extender (b)]

The chain extender (b) is a compound having, in a molecule thereof, at least two active hydrogens, which each react with an isocyanate group to be generated through deblocking of a blocked isocyanate group of the blocked isocyanate (a).

Examples of the active hydrogens, which each react with the isocyanate group, include a hydrogen atom of a hydroxyl group, a hydrogen atom of an amino group, and a hydrogen atom of a thiol group. Accordingly, the chain extender (b) preferably includes a compound having, in a molecule thereof, at least two functional groups selected from the group consisting of a hydroxyl group, an amino group, and a thiol group. In addition, from the viewpoint of reactivity, the chain extender (b) more preferably includes at least one selected from the group consisting of a polyol having at least two hydroxyl groups, a polyamine having at least two amino groups, and a polythiol having at least two thiol groups.

In addition, the chain extender (b) has a number average molecular weight Mn of preferably 1,000 or less, more preferably 500 or less. When the chain extender (b) has a number average molecular weight Mn of 1,000 or less, the chain extender (b) can efficiently react with the isocyanate group to be generated through deblocking when the photo-curable composition having been photo-cured is subjected to heat treatment as described below.

Specific examples of the chain extender (b) may include: linear diols, such as ethylene glycol, 1,3-propanediol, 1,4-butanediol, 1,5-pentanediol, 1,6-hexanediol, 1,8-octanediol, 1,9-nonanediol, and 1,10-decanediol; diols each having a branched chain, such as 2-methyl-1,3-propanediol, 2,2-dimethyl-1,3-propanediol, 2,2-diethyl-1,3-propanediol, 2-methyl-2-propyl-1,3-propanediol, 2,4-heptanediol, 1,4-dimethylolhexane, 2-ethyl-1,3-hexanediol, 2,2,4-trimethyl-1,3-pentanediol, 2-methyl-1,8-octanediol, 2-butyl-2-ethyl-1,3-propanediol, and a dimer diol; diols each having an ether group, such as diethylene glycol and propylene glycol; diols each having an alicyclic structure, such as 1,4-cyclohexanediol, 1,4-cyclohexanedimethanol, and 1,4-dihydroxyethylcyclohexane; diols each having an aromatic group, such as xylylene glycol, 1,4-dihydroxyethylbenzene, and 4,4'-methylenebis(hydroxyethylbenzene); polyols, such as glycerin, trimethylolpropane, and pentaerythritol; hydroxyamines, such as N-methylethanolamine and N-ethylethanolamine; polyamines, such as ethylenediamine, 1,3-diaminopropane, hexamethylenediamine, triethylenetetramine, diethylenetriamine, isophoronediamine, 4,4'-diaminodicyclohexylmethane, 2-hydroxyethylpropylenediamine, di-2-hydroxyethylethylenediamine, di-2-hydroxyethylpropylenediamine, 2-hydroxypropylethylenediamine, di-2-hydroxypropylethylenediamine, 4,4'-diphenylmethanediamine, methylenebis(o-chloroaniline), xylylenediamine, diphenyldiamine, tolylenediamine, hydrazine, piperazine, and N,N'-diaminopiperazine; aliphatic polythiols, such as 1,2-ethanedithiol, 1,2,3-propanetrithiol, 1,2-cyclohexanedithiol, bis(2-mercaptoethyl) ether, tetrakis(mercaptomethyl)methane, diethylene glycol bis(2-mercaptoacetate), trimethylolpropane tris(3-mercaptopropionate), trimethylolpropane tris(2-mercaptoacetate), pentaerythritol tetrakis(2-mercaptoacetate), pentaerythritol tetrakis(3-mercaptopropionate), hydroxymethyl sulfide bis(2-mercaptoacetate), hydroxymethyl sulfide bis(3-mercaptopropionate), 1,1,3,3-tetrakis (mercaptomethylthio)propane, and tris(mercaptoethylthio) methane; aromatic polythiol compounds, such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl) benzene, 1,2-bis(mercaptoethyl)benzene, 1,3-bis(mercaptoethyl)benzene, 1,4-bis(mercaptoethyl)benzene, 1,3,5-trimercaptobenzene, 1,3,5-tris(mercaptomethyl)benzene, 1,3,5-tris(mercaptomethyleneoxy)benzene, 1,3,5-tris(mercaptoethyleneoxy)benzene, 2,5-toluenedithiol, 3,4-toluenedithiol, 1,5-naphthalenedithiol, and 2,6-naphthalenedithiol; and water. Those chain extenders may be used alone or in combination thereof.

Of those, 1,4-butanediol, 1,5-pentanediol, 1,6-hexanediol, 1,8-octanediol, 1,9-nonanediol, 1,10-decanediol, 1,4-cyclohexanedimethanol, 1,4-dihydroxyethylcyclohexane, ethylenediamine, 1,3-diaminopropane, isophoronediamine, and 4,4'-diaminodicyclohexylmethane are preferred because a cured product described below has preferred physical property balance and each of those compounds is industrially inexpensively available in a large amount.

A ratio of the number of moles of the chain extender (b) to the number of moles of the blocked isocyanate (a), (number of moles of the chain extender (b)/number of moles of the blocked isocyanate (a)), is preferably 0.5 or more and 5 or less, more preferably 2 or more and 4 or less. As described below, when the photo-curable composition according to this embodiment is photo-cured and is then subjected to heat treatment, an isocyanate group is regenerated, and a reaction in which, a bond, such as a urethane bond, is generated between the isocyanate group and the chain extender (b) occurs. However, when the ratio is less than 0.5, there are tendencies that the efficiency of the reaction between the isocyanate group and the chain extender (b) is reduced, and various mechanical characteristics of the photo-cured product and the photo-cured/thermally cured product described below are reduced. In addition, when the ratio is more than 5, there are tendencies that the chain extender (b) remains unreacted excessively in a three-dimensional object, and various mechanical characteristics of the photo-cured product and the photo-cured/thermally cured product described below are reduced.

[Photo-Radical Generator (c)]

The photo-radical generator (c) is a compound which generates a radical serving as a polymerization factor when irradiated with an active energy ray, such as light having a predetermined wavelength. The photo-radical generator (c) may be a compound which is decomposed to generate a radical when irradiated with an active energy ray. Specifically, the photo-radical generator is a photo-polymerization initiator which generates a radical when irradiated with an active energy ray, such as light (e.g., an infrared ray, visible light, an ultraviolet ray, a far-ultraviolet ray, an X-ray, a charged particle beam, such as an electron beam, or radiation).

Specific examples of the photo-radical generator (c) include, but are not limited to: carbonyl compounds, such as benzoin, benzoin monomethyl ether, benzoin isopropyl ether, acetoin, benzil, benzophenone, p-methoxybenzophenone, diethoxyacetophenone, benzyl dimethyl ketal, 2,2-diethoxyacetophenone, 1-hydroxycyclohexyl phenyl ketone, methyl phenylglyoxylate, ethyl phenylglyoxylate, and 2-hydroxy-2-methyl-1-phenylpropan-1-one; sulfur compounds, such as tetramethylthiuram monosulfide and tetramethylthiuram disulfide; and acylphosphine oxides, such as 2,4,6-trimethylbenzoyl diphenylphosphine oxide.

Examples of commercially available products of the photo-radical generator include, but are not limited to: IRGACURE series, such as IRGACURE 184 and IRGACURE 819, and DAROCUR series, such as DAROCUR 1173 and DAROCUR TPO (all of which are manufactured by BASF); and KAYACURE series, such as KAYACURE DETX-S and KAYACURE CTX (all of which are manufactured by Nippon Kayaku Co., Ltd.).

The addition amount of the photo-radical generator is preferably 0.05 mass % or more and 20 mass % or less, more preferably 0.1 mass % or more and 5 mass % or less when the total amount of the photo-curable composition is defined as 100 mass %. When the addition amount is less than 0.05 mass %, the radical to be generated becomes insufficient, and the polymerization conversion rate of the photo-curable composition is reduced. As a result, the strength of the photo-cured product and the photo-cured/thermally cured product described below becomes insufficient. When the addition amount is more than 20 mass %, a large part of light radiated to the photo-curable composition is absorbed by the photo-radical generator (c), which exists excessively, and the light may not reach an inside of the curable composition.

Therefore, there is a risk in that the polymerization conversion rate of the photo-curable composition in the inside thereof is reduced.

[Other Components]

(Reactive Diluent (d))

The photo-curable composition according to this embodiment may further include a reactive diluent (d). When the reactive diluent (d) is incorporated in the photo-curable composition, the viscosity of the photo-curable composition can be reduced. In addition, the mechanical characteristics and the thermal characteristics of the photo-cured product and the photo-cured/thermally cured product described below can be controlled.

The reactive diluent (d) is preferably a monomer and/or oligomer having a radically and/or cationically polymerizable group.

Examples of the monomer having a radically polymerizable group include a (meth)acrylate-based monomer, a styrene-based monomer, acrylonitrile, a vinyl ester-based monomer, N-vinylpyrrolidone, an acrylamide-based monomer, a conjugated diene-based monomer, a vinyl ketone-based monomer, and a vinyl halide- or vinylidene halide-based monomer.

Examples of the monomer having a cationically polymerizable group include an epoxy-based monomer, an oxetane-based monomer, and a vinyl ether-based monomer.

Of those, a (meth)acrylate-based monomer having the (meth)acryloyl group same as in the blocked isocyanate (a) out of the monomers each having a radically polymerizable group is preferred. Examples of the (meth)acrylate-based monomer may include a monofunctional (meth)acrylate, a difunctional (meth)acrylate, a tri- or more functional (meth)acrylate, a urethane (meth)acrylate oligomer, and a polyester (meth)acrylate oligomer.

Examples of the (meth)acrylate-based monomer include: monofunctional (meth)acrylates, such as methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, n-hexyl (meth)acrylate, cyclohexyl (meth)acrylate, n-heptyl (meth)acrylate, n-octyl (meth)acrylate, isooctyl (meth)acrylate, 2-ethylhexyl (meth)acrylate, nonyl (meth)acrylate, isononyl (meth)acrylate, decyl (meth)acrylate, isodecyl (meth)acrylate, dodecyl (meth)acrylate, lauryl (meth)acrylate, tridecyl (meth)acrylate, cyclohexyl (meth)acrylate, isobornyl (meth)acrylate, dicyclopentanyl (meth)acrylate, adamantyl (meth)acrylate, phenyl (meth)acrylate, tolyl (meth)acrylate, benzyl (meth)acrylate, 2-methoxyethyl (meth)acrylate, 3-methoxybutyl (meth)acrylate, 2-hydroxyethyl (meth)acrylate, 2-hydroxypropyl (meth)acrylate, and stearyl (meth)acrylate; difunctional (meth)acrylates, such as 1,4-butanediol di(meth)acrylate, 1,6-hexanediol di(meth)acrylate, 1,9-nonanediol di(meth)acrylate, tricyclodecanedimethanol di(meth)acrylate, bisphenol A (poly)ethoxy di(meth)acrylate, bisphenol A (poly)propoxy di(meth)acrylate, bisphenol F (poly)ethoxy di(meth)acrylate, and ethylene glycol di(meth)acrylate; and tri- or more functional (meth)acrylates, such as ditrimethylolpropane tetra(meth)acrylate, trimethylolpropane tri(meth)acrylate, trimethyloloctane tri(meth)acrylate, trimethylolpropane polyethoxy tri(meth)acrylate, trimethylolpropane (poly)propoxy tri(meth)acrylate, trimethylolpropane (poly)ethoxy (poly)propoxy tri(meth)acrylate, pentaerythritol tri(meth)acrylate, pentaerythritol polyethoxy tetra(meth)acrylate, pentaerythritol (poly)propoxy tetra(meth)acrylate, pentaerythritol tetra(meth)acrylate, dipentaerythritol tetra(meth)acrylate, dipentaerythritol penta(meth)acrylate, dipentaerythritol hexa(meth)acrylate, tris[(meth)acryloyloxyethyl]isocyanurate, and caprolactone-modified tris[(meth)acryloyloxyethyl]isocyanurate.

Examples of the urethane (meth)acrylate oligomer include, but are not limited to, a polycarbonate-based urethane (meth)acrylate, a polyester-based urethane (meth)acrylate, a polyether-based urethane (meth)acrylate, and a caprolactone-based urethane (meth)acrylate. The urethane (meth)acrylate oligomer may be obtained by, for example, subjecting an isocyanate compound, which is obtained through a reaction between a polyol and a diisocyanate, and a (meth)acrylate monomer having a hydroxyl group to a reaction. Examples of the polyol include a polycarbonate diol, a polyester polyol, a polyether polyol, and a polycaprolactone polyol.

The polyester acrylate oligomer is obtained by, for example, obtaining a polyester oligomer having hydroxyl groups at both ends thereof through condensation between a polycarboxylic acid and a polyol, and then esterifying the hydroxyl groups at both the ends with acrylic acid.

With regard to the addition amount of the reactive diluent (d), the reactive diluent (d) may be added in an appropriate amount as long as the effects of the present invention are not impaired so that desired values for the viscosity and the curing speed of the photo-curable composition, and desired values for the mechanical and thermal characteristics of the cured product are obtained.

(Photoacid Generator (e))

The photo-curable composition according to this embodiment may further include a photoacid generator (e) when the photo-curable composition includes the monomer or oligomer having a cationically polymerizable group as the reactive diluent (d).

Specific examples of the photoacid generator (e) include, but are not limited to, a trichloromethyl-s-triazine, a sulfonium salt, an iodonium salt, a quaternary ammonium salt, a diazomethane compound, an imidosulfonate compound, and an oxime sulfonate compound.

(Other Additives)

In addition, as long as the effects of the present invention are not impaired, the photo-curable composition according to this embodiment may include, as required, one kind or two or more kinds of additives selected from, for example, a colorant, such as a pigment or a dye, a defoamer, a leveling agent, a thickener, a flame retardant, an antioxidant, an inorganic filler (cross-linked polymer particles, silica, glass powder, ceramics powder, metal powder, or the like), and a modifier resin (a thermoplastic resin, thermoplastic resin particles, rubber particles, or the like) in an appropriate amount.

In addition, the photo-curable composition according to this embodiment may include, as required, in addition to the photo-radical generator (c), a photoinitiation auxiliary or a sensitizer. Examples of the photoinitiation auxiliary or the sensitizer include, but are not limited to, a benzoin compound, an acetophenone compound, an anthraquinone compound, a thioxanthone compound, a ketal compound, a benzophenone compound, a tertiary amine compound, and a xanthone compound.

Third Embodiment

A resin (photo-cured product) according to a third embodiment of the present invention is described.

The resin (photo-cured product) according to this embodiment is a resin in a solid state obtained by irradiating the photo-curable composition according to the second embodiment with an active energy ray, such as light having a predetermined wavelength. The resin (photo-cured product) according to this embodiment includes a repeating structural unit represented by the following general formula (4).

0.001 J/cm2, there is a risk in that the photo-curable composition is not cured sufficiently. When the exposure amount is more than 10 J/cm2, an irradiation time period is prolonged, and productivity is reduced.

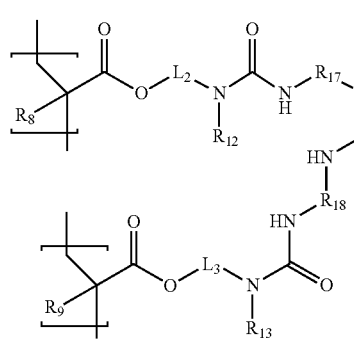
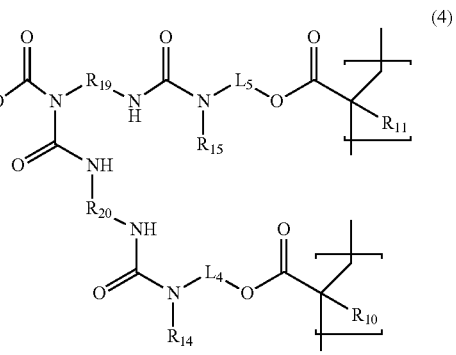

(4)

In the general formula (4), $R_5$, $R_9$, $R_{10}$, and $R_{11}$ each independently represent a hydrogen atom or a methyl group, $R_{12}$, $R_{13}$, $R_{14}$, and $R_{15}$ each independently represent a hydrocarbon group having 1 to 10 carbon atoms which may have a substituent, $L_2$, $L_3$, $L_4$, and $L_5$ each independently represent a divalent hydrocarbon group having 1 to 10 carbon atoms which may have a substituent, $R_{16a}$, $R_{16b}$, $R_{17}$, $R_{18}$, $R_{19}$, and $R_{20}$ each independently represent a divalent hydrocarbon group having 1 to 20 carbon atoms which may have a substituent, $Y_2$ represents a divalent linking group, and "b" represents an integer of 1 or more and 99 or less.

When any one of $L_2$, $L_3$, $L_4$, $L_5$, $R_{12}$, $R_{13}$, $R_{14}$, $R_{15}$, $R_{16a}$, $R_{16b}$, $R_{17}$, $R_{18}$, $R_{19}$, and $R_{20}$ in the general formula (4) has a substituent, the substituent may be a substituent including a carbon atom. However, in such case, an atom of the substituent which is bonded to each of $L_2$, $L_3$, $L_4$, $L_5$, $R_{3a}$, $R_{13}$, $R_{14}$, $R_{15}$, $R_{16a}$, $R_{16b}$, $R_{17}$, $R_{18}$, $R_{19}$, and $R_{20}$ is an atom other than the carbon atom. In addition, in such case, the number of carbon atoms included in the substituent is not included in the number of carbon atoms of the "hydrocarbon group".

In the general formula (4), $R_{12}$, $R_{13}$, $R_{14}$, and $R_{15}$ each preferably represent a group selected from the group consisting of a tert-butyl group, a tert-pentyl group, and a tert-hexyl group.

In the general formula (4), $L_2$, $L_3$, $L_4$, and $L_5$ each preferably represent an ethylene group or a propylene group.

In the general formula (4), $Y_2$ preferably represents at least one divalent linking group selected from the group consisting of groups represented by the formulae (B1) to (B3).

The active energy ray to be radiated to the photo-curable composition is not particularly limited as long as the active energy ray can cure the photo-curable composition according to this embodiment. Specific examples of the active energy ray include: electromagnetic waves, such as an ultraviolet ray, visible light, an infrared ray, an X-ray, a gamma ray, and laser light; and particle beams, such as an alpha ray, a beta ray, and an electron beam. Of those, an ultraviolet ray is most preferred in terms of an absorption wavelength of the photo-radical generator (c) to be used and facility introduction cost. An exposure amount is not particularly limited, but is preferably 0.001 J/cm2 or more and 10 J/cm2 or less. When the exposure amount is less than In addition, the photo-curable composition according to this embodiment can be suitably used for a method of manufacturing a three-dimensional object by stereolithography. A method of manufacturing a three-dimensional object including using the photo-curable composition according to this embodiment is described below.

As the stereolithography, a conventionally known method may be used. That is, the method of manufacturing a three-dimensional object according to this embodiment is a method including repeatedly performing a step of curing the photo-curable composition according to this embodiment layer by layer by selectively radiating the active energy ray, such as light, to the photo-curable composition, to thereby manufacture a three-dimensional object.

In the step of curing the photo-curable composition layer by layer, the active energy ray is selectively radiated to the photo-curable composition based on slice data of a three-dimensional object to be created. A method of radiating the active energy ray to the photo-curable composition is not particularly limited. For example, when light is radiated as the active energy ray, the following methods may be adopted. As a first method, there is given a method involving using light focused to a spot, such as laser light, and two-dimensionally scanning the photo-curable composition with the light. In this case, the two-dimensional scanning may be performed in a point drawing mode or a line drawing mode. As a second method, there is given a surface exposure mode involving radiating light in a shape of sectional data through use of, for example, a projector. In this case, the active energy ray may be radiated in a planar manner through a planar drawing mask formed by arranging a plurality of micro light shutters, such as liquid crystal shutters or digital micro mirror shutters.

In this step, after the three-dimensional object is obtained by the stereolithography, a surface of the obtained three-dimensional object may be washed with a washing agent, such as an organic solvent. In addition, the obtained three-dimensional object may be subjected to post-curing involving irradiating the three-dimensional object with light to cure a residual component, which may remain unreacted on the surface or in the inside of the three-dimensional object.

Fourth Embodiment

A resin (photo-cured/thermally cured product) according to a fourth embodiment of the present invention is described.

(Photo-Cured/Thermally Cured Product)

The resin (photo-cured/thermally cured product) according to this embodiment is a resin in a solid state obtained by subjecting the resin (photo-cured product) according to the third embodiment to heat treatment. The resin (photo-cured/thermally cured product) according to this embodiment includes a repeating structural unit represented by the following general formula (5) and a repeating structural unit represented by the following general formula (6).

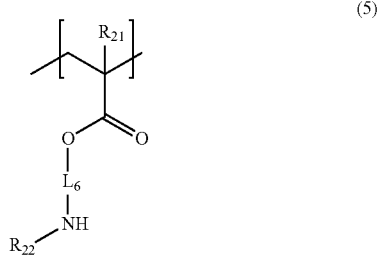

(5)

In the general formula (5), $R_{21}$ represents a hydrogen atom or a methyl group, $R_{22}$ represents a hydrocarbon group having 1 to 10 carbon atoms which may have a substituent, and $L_6$ represents a divalent hydrocarbon group having 1 to 10 carbon atoms which may have a substituent.

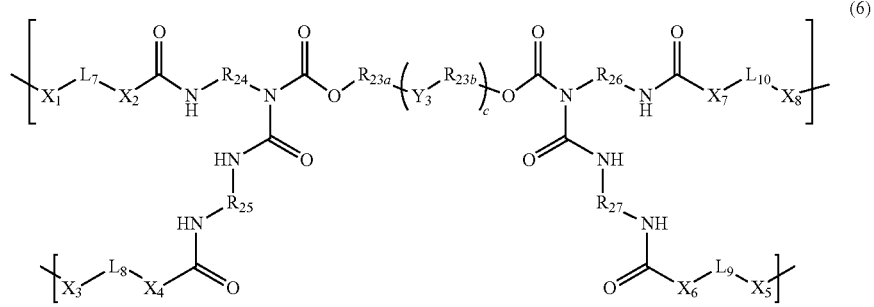

(6)

In the general formula (6), $L_7$, $L_5$, $L_9$, and $L_{10}$ each independently represent a divalent hydrocarbon group having 1 to 10 carbon atoms which may have a substituent, $R_{23a}$, $R_{23b}$, $R_{24}$, $R_{25}$, $R_{26}$, and $R_{27}$ each independently represent a divalent hydrocarbon group having 1 to 20 carbon atoms which may have a substituent, $Y_3$ represents a divalent linking group, c represents an integer of 1 or more and 99 or less, and $X_1$, $X_2$, $X_3$, $X_4$, $X_5$, $X_6$, $X_7$, and $X_8$ each independently represent any one of O, S, and NH.

When any one of $L_6$, $L_7$, $L_8$, $L_9$, $L_{10}$, $R_{22}$, $R_{23a}$, $R_{23b}$, $R_{24}$, $R_{25}$, $R_{26}$, and $R_{27}$ in the general formula (5) and the general formula (6) has a substituent, the substituent may be a substituent including a carbon atom. However, in such case, an atom of the substituent which is bonded to each of $L_6$, $L_7$, $L_8$, $L_9$, $L_{10}$, $R_{22}$, $R_{23a}$, $R_{23b}$, $R_{24}$, $R_{25}$, $R_{26}$, and $R_{27}$ is an atom other than the carbon atom. In addition, in such case, the number of carbon atoms included in the substituent is not included in the number of carbon atoms of the "hydrocarbon group".

In the general formula (5), $R_{22}$ preferably represents a group selected from the group consisting of a tert-butyl group, a tert-pentyl group, and a tert-hexyl group.

In the general formula (5) and the general formula (6), $L_6$, $L_7$, $L_5$, $L_9$, and $L_{10}$ each preferably represent an ethylene group or a propylene group.

In the general formula (6), $Y_3$ preferably represents at least one divalent linking group selected from the group consisting of groups represented by the formulae (B1) to (B3).

[Mechanism for Obtaining Photo-Cured/Thermally Cured Product]

FIG. 1s a view for illustrating a reaction scheme in which the photo-curable composition according to the second embodiment is irradiated with light to provide the resin (photo-cured product) according to the third embodiment, and then the resin (photo-cured product) is subjected to heat treatment to provide the resin (photo-cured/thermally cured product) according to the fourth embodiment. The details thereof are described below. In FIGURE, the photo-curable composition includes: the blocked isocyanate (a); the chain extender (b); and the photo-radical generator (c).

When the photo-curable composition according to this embodiment illustrated in (A) of FIG. 1s irradiated with light (e.g., ultraviolet ray) having a predetermined wavelength, the photo-radical generator (c) in the photo-curable composition generates a radical. Then, the (meth)acryloyl groups of the blocked isocyanate (a) are subjected to a polymerization reaction, and thus the photo-curable composition is solidified. When the photo-curable composition further includes the reactive diluent (d) described above, not only a polymerization reaction between the blocked isocyanates (a), but also a polymerization reaction between the blocked isocyanate (a) and the reactive diluent (d) proceeds. With this, a photo-cured product as schematically illustrated in (B) of FIG. 1s generated.

Next, when the obtained photo-cured product is subjected to heat treatment, deblocking in which a blocking moiety (BL) derived from the blocking agent is eliminated proceeds, and an isocyanate group is regenerated as schematically illustrated in (C) of FIGURE. Then, the regenerated isocyanate group immediately reacts with the chain extender (b). With this, when the chain extender (b) has a hydroxyl group, a urethane bond is generated through a reaction between the hydroxyl group and the isocyanate group. Alternatively, when the chain extender (b) has an amino group, a urea bond is generated through a reaction between the amino group and the isocyanate group. As a result, a cured product as schematically illustrated in (D) of FIGURE is obtained.

In general, a cured product obtained through a polymerization reaction of polyfunctional (meth)acryloyl groups tends to have a high crosslinking density and low toughness. However, in the case of the photo-curable composition according to this embodiment, the deblocking occurs as described above when the photo-curable composition having been photo-cured is subjected to heat treatment. Thus, a crosslinking density obtained through crosslinking in association with the (meth)acryloyl groups is reduced. Moreover, the urethane bond or the urea bond is generated, and thus a cured product having a polyurethane structure, a polyurea structure, or a mixed structure thereof is generated. The cured product having a polyurethane structure, a polyurea structure, or a mixed structure thereof has, in a molecular structure thereof, at least four blocking groups, that is, four crosslinking points. Therefore, the cured product has a high crosslinking density, and as a result, can have a higher modulus of elasticity and higher toughness than a related-art cured product.

EXAMPLES

Examples are given below in order to specifically describe the present invention, but the present invention is not limited to these Examples. In each of Examples and Comparative Example, identification of a compound, tracing of a reaction, and measurement of mechanical characteristics were performed by methods described below.

(Identification of Compound)

A compound was identified by dissolving 15 mg of a sample in 1.1 g of deuterated chloroform (CDCl3), and subjecting the resultant solution to $^1$H-NMR measurement with a nuclear magnetic resonance spectrometer JNM-ECA-400 (manufactured by JEOL Ltd.).

(Tracing of Reaction (Confirmation of Disappearance of Isocyanate Group))

A sample was measured by an attenuated total reflection method (ATR method) with a Fourier transform infrared spectrometer (Spectrum One manufactured by PerkinElmer, Inc.). An absorbance was plotted on the ordinate, and the proceeding of a reaction was confirmed based on the presence or absence of a peak around 2,260 cm−1 derived from an isocyanate group.

(Evaluation of Tensile Strength and Tensile Modulus of Elasticity)

A test piece was produced by punching a cured product having a thickness of about 300 μm into a No. 8 dumbbell shape. The test piece was measured for a tensile strength and a tensile modulus of elasticity at a test temperature of 23° C. and a tension speed of 10 mm/min with a tensile tester (product name "Strograph EII", manufactured by Toyo Seiki Seisaku-sho, Ltd.) in conformity with JIS K 7127.

(Evaluation of Toughness)

A Charpy impact strength was measured under an atmosphere of 23° C. with an impact tester (product name "digital impact tester DG-UB", manufactured by Toyo Seiki Seisaku-sho, Ltd.) in conformity with JIS K 7111.

A test piece to be used was obtained as described below. A test piece having a length of 80 mm, a width of 10 mm, and a thickness of 4 mm was produced from a cured product, and a notch having a depth of 2 mm and an angle of 45° was formed in a middle portion of the test piece.

(Synthesis of Blocked Isocyanate 1)

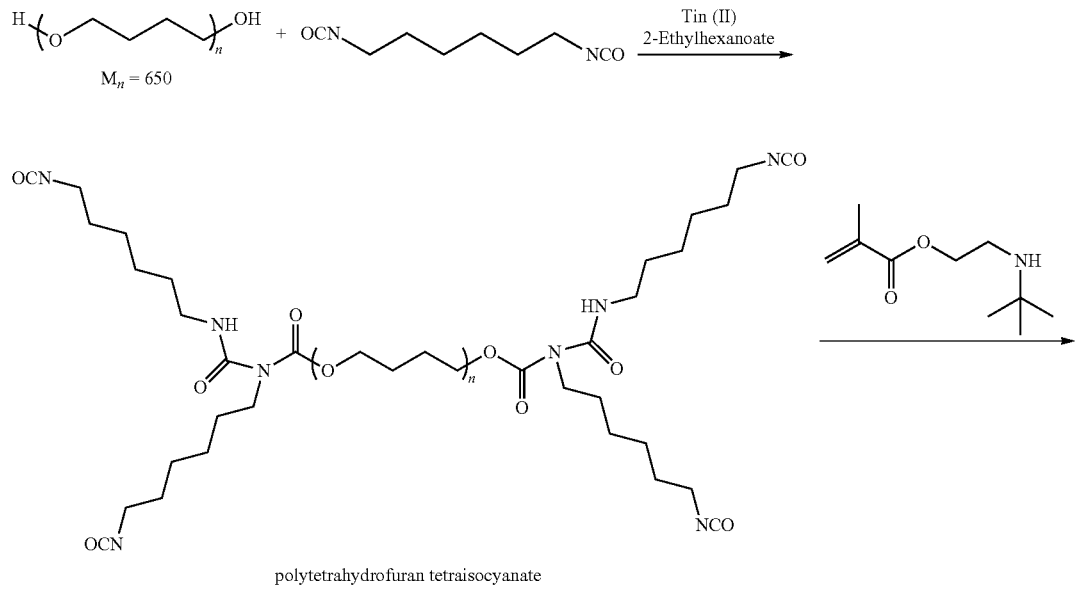

polytetrahydrofuran tetraisocyanate

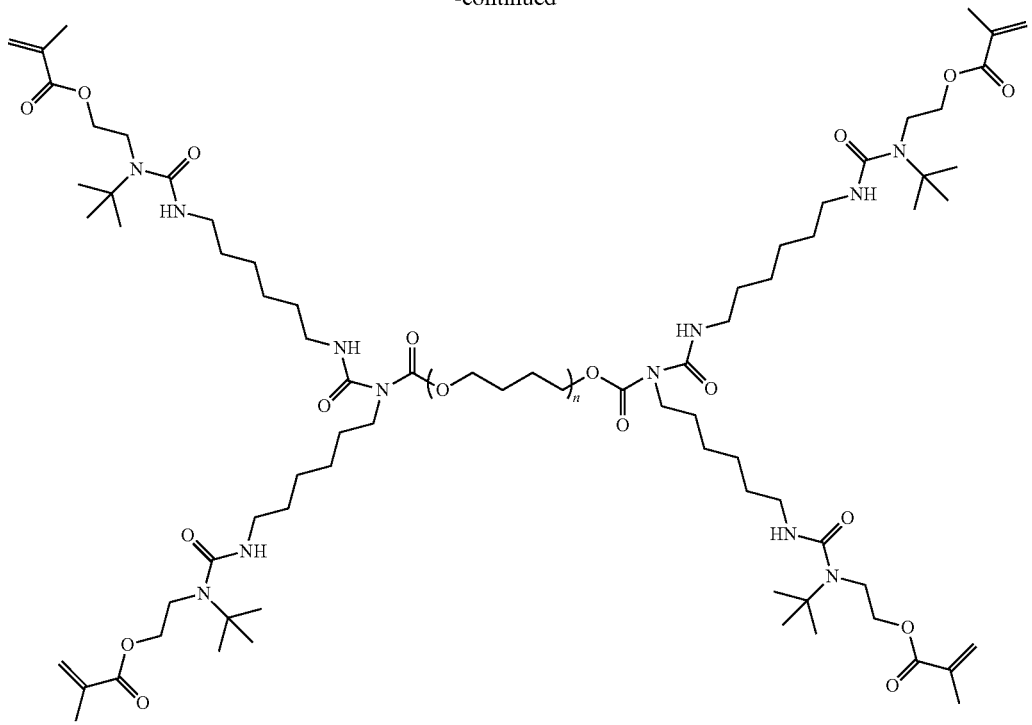

blocked isocyanate 1

Based on the scheme, a blocked isocyanate 1 was synthesized. First, polytetrahydrofuran (100 g, 154 mmol, 1.0 eq.) having a number average molecular weight Mn of 650 and hexamethylene diisocyanate (207 g, 1.23 mol, 8.0 eq.) were added to a 500 mL reactor under an argon atmosphere at room temperature, and the resultant solution was stirred. Tin(II) 2-ethylhexanoate (80 μL, cat.) was added to the solution. The temperature of the solution was increased to 80° C., and the solution was stirred at 80° C. for 8 hours. The solution was left to cool to room temperature, and was then added to hexane (4 L) vigorously stirred. The solution was stirred under the state for 15 minutes, and was then left to stand still for 15 minutes, and the upper layer (hexane layer) was removed through decantation. This operation was repeated twice more, and the lower layer was concentrated. Thus, 170 g of polytetrahydrofuran tetraisocyanate was obtained.

300 mL of dichloromethane was added to the polytetrahydrofuran tetraisocyanate thus obtained, and the resultant solution was cooled with ice while being stirred. Hydroquinone (10 mg) and 2-(tert-butylamino)ethylmethacrylate (227 g, 1.23 mol, 8.0 eq.) were added thereto slowly, and the resultant solution was stirred at room temperature for 12 hours. The solution was analyzed by infrared spectroscopy. By the above-mentioned method, it was confirmed that there was no absorption peak derived from an isocyanate.

Next, the solution was added slowly to hexane (4 L) vigorously stirred. The solution was stirred under the state for 20 minutes, and was then left to stand still for 20 minutes, and a hexane layer serving as the upper layer was removed through decantation. This operation was repeated three times more. The target lower layer was subjected to celite filtration, and was then concentrated under high vacuum. Thus, the blocked isocyanate 1 (184 g) serving as a colorless viscous liquid was obtained.

(Synthesis of Blocked Isocyanate 2)

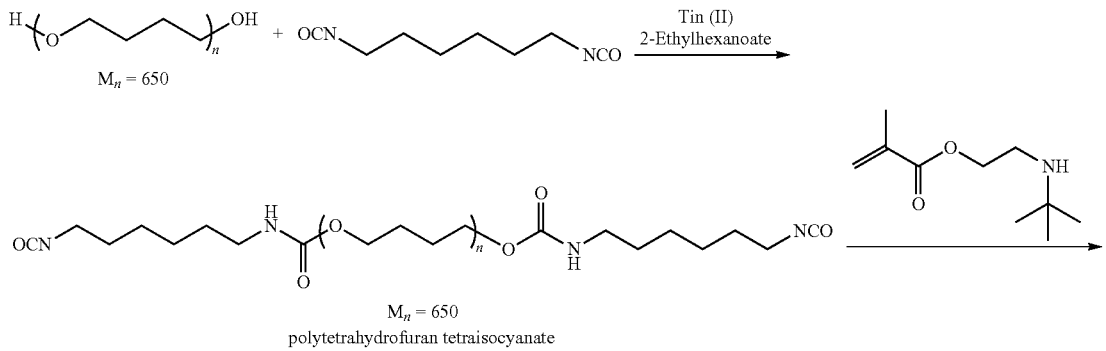

$M_n = 650$
polytetrahydrofuran tetraisocyanate

-continued

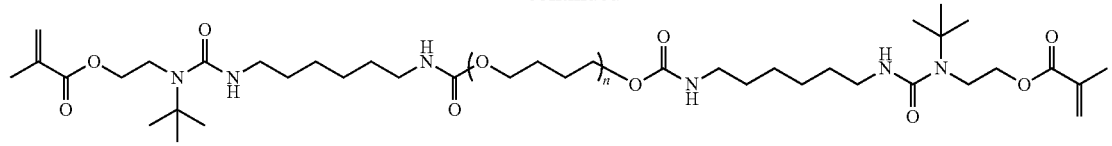

$M_n = 650$
blocked isocyanate 2

Based on the scheme, a blocked isocyanate 2 was synthesized. First, polytetrahydrofuran (100 g, 154 mmol, 1.0 eq.) having a number average molecular weight Mn of 650 and hexamethylene diisocyanate (53.5 g, 615 mmol, 4.0 eq.) were added to a 500 mL reactor under an argon atmosphere at room temperature, and the resultant solution was stirred. Tin(II) 2-ethylhexanoate (80 μL, cat.) was added to the solution. The solution was stirred at room temperature for 5 hours. The solution was added to hexane (4 L) vigorously stirred. The solution was stirred under the state for 15 minutes, and was then left to stand still, and the upper layer (hexane layer) was removed through decantation. This operation was repeated twice more, and the lower layer was concentrated. Thus, 116 g of polytetrahydrofuran diisocyanate was obtained.

300 mL of dichloromethane was added to the polytetrahydrofuran diisocyanate thus obtained, and the resultant solution was cooled with ice while being stirred. Hydroquinone (10 mg) and 2-(tert-butylamino)ethylmethacrylate (114 g, 615 mmol, 4.0 eq.) were added thereto slowly, and the resultant solution was stirred at room temperature for 12 hours. The solution was analyzed by infrared spectroscopy. By the above-mentioned method, it was confirmed that there was no absorption peak derived from an isocyanate.

Next, the solution was added slowly to hexane (4 L) vigorously stirred. The solution was stirred under the state for 20 minutes, and was then left to stand still, and a hexane layer serving as the upper layer was removed through decantation. This operation was repeated three times more. The target lower layer was subjected to celite filtration, and was then concentrated under high vacuum. Thus, the blocked isocyanate 2 (141 g) serving as a colorless viscous liquid was obtained.

Examples 1 to 4

<Preparation of Photo-Curable Compositions 1 to 4>

The blocked isocyanate 1 and/or the blocked isocyanate 2 serving as a blocked isocyanate, 4,4'-diaminodiphenylmethane serving as a chain extender, isobornyl methacrylate serving as a reactive diluent, and bis(2,4,6-trimethylbenzoyl)-phenylphosphine oxide serving as a photo-radical generator in amounts shown in Table 1 were loaded in a light shielding bottle, and stirred to uniformity with a stirring deaerator. Thus, each of photo-curable compositions 1 to 4 was prepared.

<Production of Photo-Cured Products 1 to 4>

Film

Each of the photo-curable compositions 1 to 4 was poured between two quartz glass sheets between which a gap was formed with a 300 μm spacer. An ultraviolet ray at 5 mW/cm2 was radiated to each of the photo-curable compositions 1 to 4 for 120 seconds with an ultraviolet ray irradiation device (manufactured by Hoya-Schott Corporation, product name, UV Light Source EX250). Thus, a photo-cured product in a film shape was obtained.

Test Piece

Each of the photo-curable compositions 1 to 4 was poured into a mold measuring 80 mm×10 mm×4 mm which was sandwiched between glasses from both surfaces thereof. An ultraviolet ray at 5 mW/cm2 was first radiated to both surfaces for 120 seconds per surface, and was then radiated thereto for 360 seconds per surface with an ultraviolet ray irradiation device (manufactured by Hoya-Schott Corporation, product name, UV Light Source EX250). Thus, each of photo-cured products 1 to 4 in a test piece shape was obtained.

<Production of Photo-Cured/Thermally Cured Products 1 to 4>

Each of the photo-cured products 1 to 4 was placed in an oven at 125° C. and subjected to heat treatment for 4 hours. Thus, each of photo-cured/thermally cured products 1 to 4 was obtained.

<Evaluation of Mechanical Characteristics of Photo-Cured/Thermally Cured Products 1 to 4>

The tensile modulus of elasticity, the tensile strength, and the Charpy impact strength of each of the photo-cured/thermally cured products 1 to 4 were measured by the above-mentioned methods. The results are shown in Examples 1 to 4 of Table 1.

Comparative Example

The preparation of a photo-curable resin, the production of a photo-cured product, the production of a photo-cured/thermally cured product, and the evaluation of the mechanical characteristics of the photo-cured/thermally cured product were performed in the same manner as in Examples except that only the blocked isocyanate 2 was used as a blocked isocyanate. The results are shown in Comparative Example 1 of

TABLE 1

| | Composition of photo-curable composition | | | | Result of tensile test | | Result of impact strength test |
| --- | --- | --- | --- | --- | --- | --- | --- |
| | Blocked isocyanate | Chain extender | Reactive diluent | Photo-polymerization initiator | Modulus of elasticity Gpa | Tensile strength Mpa | Charpy impact strength kJ/m² |
| Example 1 | Blocked isocyanate 1 10.7 parts by weight  Blocked isocyanate 2 42.7 parts by weight | 4,4'-Diaminodiphenylmethane 6.2 parts by weight | Isobornyl methacrylate 39.7 parts by weight | Bis(2,4,6-trimethylbenzoyl)-phenylphosphine oxide 0.7 part by weight | 0.66 | 28.3 | 7.3 |

TABLE 1-continued

| | Composition of photo-curable composition | | | | Result of tensile test | | Result of impact strength test |
| | | | | | Modulus of elasticity Gpa | Tensile strength Mpa | Charpy impact strength kJ/m² |
| | Blocked isocyanate | Chain extender | Reactive diluent | Photo-polymerization initiator | | | |
|---|---|---|---|---|---|---|---|
| Example 2 | Blocked isocyanate 1 26.7 parts by weight | Blocked isocyanate 2 26.7 parts by weight | 4,4'-Diaminodiphenylmethane 6.2 parts by weight | Isobornyl methacrylate 39.7 parts by weight | Bis(2,4,6-trimethylbenzoyl)-phenylphosphine oxide 0.7 part by weight | 0.92 | 31.4 | 6.6 |
| Example 3 | Blocked isocyanate 1 40.1 parts by weight | Blocked isocyanate 2 13.3 parts by weight | 4,4'-Diaminodiphenylmethane 6.2 parts by weight | Isobornyl methacrylate 39.7 parts by weight | Bis(2,4,6-trimethylbenzoyl)-phenylphosphine oxide 0.7 part by weight | 1.03 | 37.5 | 6.4 |
| Example 4 | Blocked isocyanate 1 53.4 parts by weight | Blocked isocyanate 2 0 parts by weight | 4,4'-Diaminodiphenylmethane 6.2 parts by weight | Isobornyl methacrylate 39.7 parts by weight | Bis(2,4,6-trimethylbenzoyl)-phenylphosphine oxide 0.7 part by weight | 1.21 | 38.8 | 6.7 |
| Comparative Example 1 | Blocked isocyanate 1 0 parts by weight | Blocked isocyanate 2 53.4 parts by weight | 4,4'-Diaminodiphenylmethane 6.2 parts by weight | Isobornyl methacrylate 39.7 parts by weight | Bis(2,4,6-trimethylbenzoyl)-phenylphosphine oxide 0.7 part by weight | 0.45 | 21.3 | 1.0 |

<Summary of Results>

As shown in Table 1, with the photo-curable compositions of Examples 1 to 4, the photo-cured/thermally cured products each having a higher modulus of elasticity, higher tensile strength, and higher Charpy impact strength than the photo-cured/thermally cured product formed with the photo-curable composition of Comparative Example were able to be formed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-226771, filed Nov. 27, 2017, which is hereby incorporated by reference herein in its entirety.

What is claimed is:

1. A blocked isocyanate represented by general formula (1):

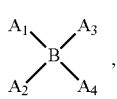
(1)

wherein, in the general formula (1), $A_1$ to $A_4$ each independently represent a structure represented by general formula (2), and B represents a structure represented by general formula (3):

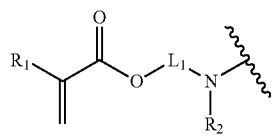
(2)

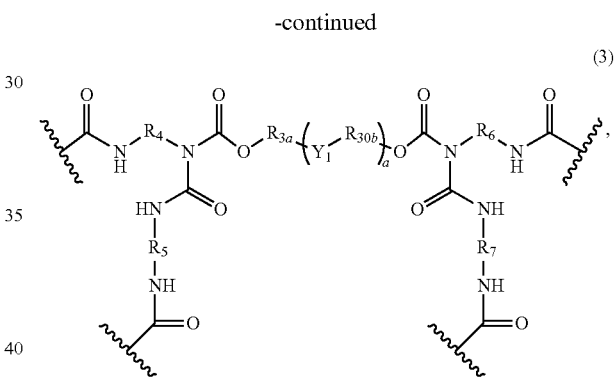
(3)

wherein, in the general formula (2), $R_1$ represents a hydrogen atom or a methyl group, $R_2$ represents a group selected from the group consisting of a tert-butyl group, a tert-pentyl group, and a tert-hexyl group, and $L_1$ represents an ethylene group or a propylene group, and wherein, in the general formula (3), $R_{3a}$, $R_{3b}$, $R_4$, $R_5$, $R_6$, and $R_7$ each independently represent an optionally substituted divalent hydrocarbon group having 1 to 20 carbon atoms, $Y_1$ represents a divalent linking group, and "a" represents an integer of 1 to 99.

2. The blocked isocyanate according to claim 1, wherein, in the general formula (3), $Y_1$ represents at least one divalent linking group selected from the group consisting of groups represented by formulae (B1) to (B3):

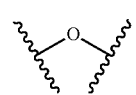
(B1)

(B2)

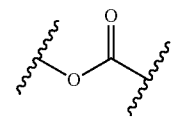

(B3)

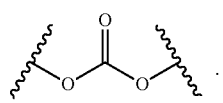

(3)

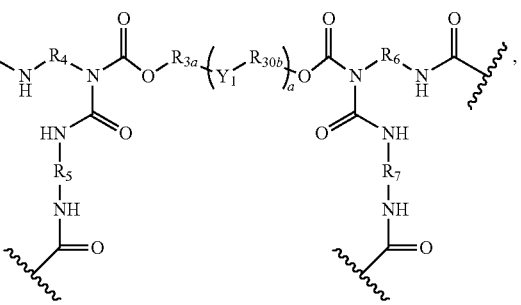

3. The blocked isocyanate according to claim 1, wherein, in the general formula (1), $A_1$ to $A_4$ are identical to one another.

4. A photo-curable composition comprising:
a blocked isocyanate represented by general formula (1);
a chain extender, wherein the chain extender comprises a compound having, in a molecule thereof, at least two functional groups selected from the group consisting of a hydroxyl group, an amino group, and a thiol group; and
a photo-radical generator:

(1)

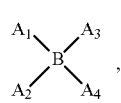

wherein, in the general formula (1), $A_1$ to $A_4$ each independently represent a structure represented by general formula (2), and B represents a structure represented by general formula (3):

(2)

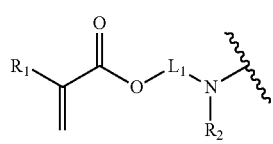

wherein, in the general formula (2), $R_1$ represents a hydrogen atom or a methyl group, $R_2$ represents a group selected from the group consisting of a tert-butyl group, a tert-pentyl group, and a tert-hexyl group, and $L_1$ represents an ethylene group or a propylene group, and wherein, in the general formula (3), $R_{3a}$, $R_{3b}$, $R_4$, $R_5$, $R_6$, and $R_7$ each independently represent an optionally substituted divalent hydrocarbon group having 1 to 20 carbon atoms, $Y_1$ represents a divalent linking group, and "a" represents an integer of 1 to 99.

5. The photo-curable composition according to claim 4, further comprising a reactive diluent.

6. The photo-curable composition according to claim 5, wherein the reactive diluent comprises a compound having one of an acryloyl group and a methacryloyl group.

7. The photo-curable composition according to claim 4, wherein a blending ratio of the blocked isocyanate is 5 mass % to 90 mass % of the photo-curable composition.

8. The photo-curable composition according to claim 4, wherein the photo-curable composition is used for creating a three-dimensional object.

9. A resin comprising a repeating structural unit represented by general formula (4):

(4)

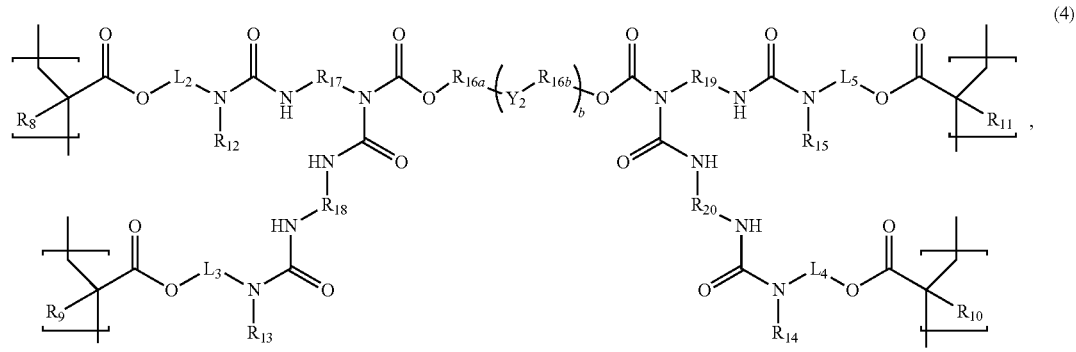

wherein, in the general formula (4), $R_8$, $R_9$, $R_{10}$, and $R_{11}$ each independently represent a hydrogen atom or a methyl group, $R_{12}$, $R_{13}$, $R_{14}$, and $R_{15}$ each independently represent a group selected from the group consisting of a tert-butyl group, a tert-pentyl group, and a tert-hexyl group, $L_2$, $L_3$, $L_4$, and $L_5$ each independently represent an ethylene group or a propylene group, $R_{16a}$, $R_{16b}$, $R_{17}$, $R_{18}$, $R_{19}$, and Rao each independently represent an optionally substituted divalent hydrocarbon group having 1 to 20 carbon atoms, $Y_2$ represents a divalent linking group, and "b" represents an integer of 1 to 99.

10. A method of manufacturing a three-dimensional object comprising photo-curing a photo-curable composition comprising: a blocked isocyanate represented by the general formula (1); a chain extender; and a photo-radical generator layer by layer based on slice data to create a three-dimensional object:

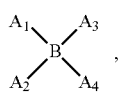
(1)

wherein, in the general formula (1), $A_1$ to $A_4$ each independently represent a structure represented by general formula (2), and B represents a structure represented by general formula (3);

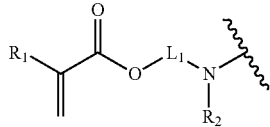
(2)

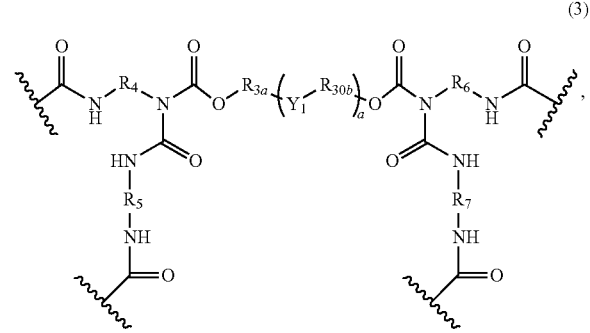
(3)

wherein, in the general formula (2), $R_1$ represents a hydrogen atom or a methyl group, $R_2$ represents a group selected from the group consisting of a tert-butyl group, a tert-pentyl group, and a tert-hexyl group, and $L_1$ represents an ethylene group or a propylene group, and wherein, in the general formula (3), $R_{3a}$, $R_{3b}$, $R_4$, $R_5$, $R_6$, and $R_7$ each independently represent an optionally substituted divalent hydrocarbon group having 1 to 20 carbon atoms, $Y_1$ represents a divalent linking group, and "a" represents an integer of 1 to 99.

* * * * *